(12) United States Patent
Moss

(10) Patent No.: US 10,384,982 B2
(45) Date of Patent: Aug. 20, 2019

(54) WASTE MATERIAL PROCESSING SYSTEM

(71) Applicant: Planet Found Energy Development, LLC, Pocomoke City, MD (US)

(72) Inventor: Andrew Moss, Pocomoke City, MD (US)

(73) Assignee: PLANET FOUND ENERGY DEVELOPMENT, LLC, Pocomoke City, MD (US)

( * ) Notice: Subject to any disclaimer, the term of this patent is extended or adjusted under 35 U.S.C. 154(b) by 126 days.

(21) Appl. No.: 15/259,859

(22) Filed: Sep. 8, 2016

(65) Prior Publication Data

US 2017/0066691 A1    Mar. 9, 2017

Related U.S. Application Data

(60) Provisional application No. 62/215,859, filed on Sep. 9, 2015.

(51) Int. Cl.
*C05B 17/00* (2006.01)
*C02F 3/28* (2006.01)
(Continued)

(52) U.S. Cl.
CPC .......... *C05B 17/00* (2013.01); *C05F 17/0018* (2013.01); *C05F 17/0027* (2013.01);
(Continued)

(58) Field of Classification Search
CPC ....... C05B 17/00; C12M 23/58; C12M 41/12; C12M 43/08; C12M 41/40; C12M 41/26;
(Continued)

(56) References Cited

U.S. PATENT DOCUMENTS 3,971,720 A    7/1976  Swanson et al.
4,065,287 A   12/1977  Roth
(Continued)

OTHER PUBLICATIONS

Stephen Dvorak, DVO Inc. "DVO Anaerobic Digester, Poultry Flow Diagram". 2013. www.DVOinc.net. 1 Page.
(Continued)

*Primary Examiner* — Fred Prince
(74) *Attorney, Agent, or Firm* — Global IP Counselors, LLP

(57) ABSTRACT

An organic waste material processing system includes a waste material holding tank and a slurry-producing device configured to process organic waste material into a slurry. A waste processing section has at least one pressurizeable tank connected to the waste material holding tank receiving slurry therefrom. The pressurizeable tank includes a slurry temperature adjusting part and a first hydrocarbon capturing structure configured to capture hydrocarbon vapors produced by the slurry at a predetermined temperature. A hydrocarbon vapor processing section collects captured hydrocarbon vapors from the waste processing section such that an electric power producing apparatus generates electricity using collected hydrocarbon vapor and provides electric power to at least the pretreatment section and the waste processing section. A waste post-processing section is configured to receive processed slurry produce salable organic materials, nutrient enhanced media and recycled water.

72 Claims, 9 Drawing Sheets

(51) Int. Cl.
   *C05F 17/00* (2006.01)
   *C12M 1/00* (2006.01)
   *C12M 1/34* (2006.01)
   *C12M 1/107* (2006.01)
   *C05F 17/02* (2006.01)

(52) U.S. Cl.
   CPC ...... *C05F 17/0036* (2013.01); *C05F 17/0045* (2013.01); *C05F 17/0063* (2013.01); *C05F 17/0258* (2013.01); *C12M 21/04* (2013.01); *C12M 23/58* (2013.01); *C12M 41/12* (2013.01); *C12M 41/26* (2013.01); *C12M 41/40* (2013.01); *C12M 43/08* (2013.01); *C02F 3/28* (2013.01); *Y02P 20/145* (2015.11); *Y02W 30/43* (2015.05); *Y02W 30/47* (2015.05)

(58) Field of Classification Search
   CPC . C12M 21/04; C05F 17/0027; C05F 17/0063; C05F 17/0018; C05F 17/0036; C05F 17/0045; C05F 17/0258; Y02W 30/47; Y02W 30/43; Y02P 20/145; C02F 3/286; C02F 11/04
   USPC ....... 210/603, 612, 613, 614, 631, 173, 175, 210/198.1, 252, 259; 71/10, 11, 21, 23
   See application file for complete search history.

(56) References Cited

U.S. PATENT DOCUMENTS

| | | | |
|---|---|---|---|
| 4,233,155 A | 11/1980 | Hawkes et al. | |
| 4,252,901 A * | 2/1981 | Fischer | C12M 21/04 210/603 |
| 5,411,567 A | 5/1995 | Ueotani et al. | |
| 5,942,116 A | 8/1999 | Clark et al. | |
| 5,976,373 A | 11/1999 | Trocciola et al. | |
| 6,254,654 B1 | 7/2001 | Van Barneveld | |
| 6,299,774 B1 | 10/2001 | Ainsworth | |
| 6,409,788 B1 | 6/2002 | Sower | |
| 6,497,741 B2 | 12/2002 | Sower | |
| 6,569,332 B2 | 5/2003 | Ainsworth et al. | |
| 6,682,578 B2 | 1/2004 | Sower | |
| 6,692,642 B2 | 2/2004 | Josse et al. | |
| 6,824,682 B2 | 11/2004 | Branson | |
| 6,863,826 B2 | 3/2005 | Sheets | |
| 6,878,179 B2 | 4/2005 | Porubcan | |
| 6,890,438 B2 | 5/2005 | Shankar et al. | |
| 6,893,567 B1 | 5/2005 | Vanotti et al. | |
| 7,044,994 B2 | 5/2006 | Porubcan | |
| 7,135,116 B2 | 11/2006 | Haggerty | |
| 7,156,999 B2 | 1/2007 | Blais et al. | |
| 7,169,821 B2 | 1/2007 | Branson | |
| 7,320,753 B2 | 1/2008 | Roos | |
| 7,442,224 B2 | 10/2008 | Porubcan | |
| 7,604,742 B2 | 10/2009 | Shankar et al. | |
| 7,662,205 B2 | 2/2010 | Burnham | |
| 7,674,379 B2 | 3/2010 | Vanotti et al. | |
| 7,785,467 B2 | 8/2010 | Logan et al. | |
| 7,789,931 B2 | 9/2010 | Burnham et al. | |
| 7,927,848 B2 | 4/2011 | Holm et al. | |
| 7,947,104 B2 | 5/2011 | Burnham et al. | |
| 8,057,569 B2 | 11/2011 | Burnham et al. | |
| 8,062,405 B1 | 11/2011 | Reiter et al. | |
| 8,110,106 B2 | 2/2012 | Allen et al. | |
| 8,158,089 B2 | 4/2012 | Zhang et al. | |
| 8,202,721 B2 | 6/2012 | Dvorak | |
| 8,246,828 B2 | 8/2012 | Cheong et al. | |
| 8,313,921 B2 | 11/2012 | Kraemer et al. | |
| 8,394,271 B2 | 3/2013 | Dvorak | |
| 8,409,439 B1 | 4/2013 | Tovani et al. | |
| 8,414,808 B2 | 4/2013 | Dvorak et al. | |
| 8,465,645 B2 | 6/2013 | Sassow | |
| 8,470,177 B2 | 6/2013 | Dvorak | |
| 8,557,013 B2 | 10/2013 | Burnham et al. | |
| 8,568,591 B2 | 10/2013 | Knoop | |
| 8,613,894 B2 | 12/2013 | Zhao et al. | |
| 8,623,110 B2 | 1/2014 | Bevans et al. | |
| 8,662,791 B2 | 3/2014 | Allen et al. | |
| 8,673,046 B1 | 3/2014 | Szogi et al. | |
| 8,747,672 B2 | 6/2014 | Bowers | |
| 8,822,379 B2 | 9/2014 | Goodwin | |
| 8,835,155 B2 | 9/2014 | Dvorak | |
| 8,864,992 B2 | 10/2014 | Barak | |
| 8,911,627 B2 | 12/2014 | Johnson | |
| 8,920,733 B2 | 12/2014 | Burnham et al. | |
| 8,936,663 B2 | 1/2015 | Kpomblekou-Ademawo | |
| 8,992,654 B2 | 3/2015 | Dahms et al. | |
| 9,005,918 B2 | 4/2015 | Dvorak et al. | |
| 9,023,209 B2 | 5/2015 | Ott | |
| 9,027,359 B2 | 5/2015 | O'Brien et al. | |
| 9,121,644 B2 | 9/2015 | Badger et al. | |
| 9,133,068 B2 | 9/2015 | Callendrello et al. | |
| 9,206,088 B2 | 12/2015 | Harman | |
| 9,328,030 B2 | 5/2016 | Burnham et al. | |
| 9,334,166 B2 | 5/2016 | Bowers | |
| 9,339,760 B2 | 5/2016 | Kennedy et al. | |
| 2002/0079266 A1* | 6/2002 | Ainsworth | C02F 3/28 210/603 |
| 2009/0017512 A1* | 1/2009 | May | C12M 21/12 435/165 |
| 2009/0107913 A1* | 4/2009 | Johnson | C05F 5/008 210/604 |
| 2009/0193863 A1 | 8/2009 | Szogi et al. | |
| 2010/0112242 A1* | 5/2010 | Medoff | C08H 8/00 428/22 |
| 2010/0264079 A1* | 10/2010 | Begin | C05F 17/0018 210/603 |
| 2010/0319423 A1 | 12/2010 | Thomsen et al. | |
| 2011/0003357 A1* | 1/2011 | Barclay | A01G 33/00 435/167 |
| 2011/0154838 A1 | 6/2011 | O'Brien et al. | |
| 2011/0200954 A1* | 8/2011 | Sassow | C12M 21/04 431/2 |
| 2011/0265532 A1 | 11/2011 | Burnham et al. | |
| 2011/0286799 A1 | 11/2011 | De La Garza et al. | |
| 2011/0289992 A1 | 12/2011 | Allen | |
| 2012/0125840 A1* | 5/2012 | Smith | C12M 41/48 210/631 |
| 2012/0318745 A1 | 12/2012 | Bowers | |
| 2013/0019645 A1 | 1/2013 | Crabtree et al. | |
| 2013/0283872 A1 | 10/2013 | Bisson et al. | |
| 2014/0109637 A1 | 4/2014 | Bevans et al. | |
| 2014/0147910 A1 | 5/2014 | Bowers | |
| 2014/0178281 A1 | 6/2014 | Bowers | |
| 2014/0263040 A1 | 9/2014 | Smith | |
| 2014/0349365 A1 | 11/2014 | Bowers | |
| 2014/0370566 A1* | 12/2014 | Hughes | C12M 47/10 435/168 |
| 2015/0060356 A1 | 3/2015 | Barry | |
| 2015/0076058 A1 | 3/2015 | Brooks et al. | |
| 2015/0197458 A1 | 7/2015 | Thomsen et al. | |
| 2015/0259259 A1 | 9/2015 | Bhalla et al. | |
| 2015/0274556 A1 | 10/2015 | Church et al. | |
| 2015/0368166 A1 | 12/2015 | Callendrello et al. | |

OTHER PUBLICATIONS

Jingwei MA, et al. "Review of Emerging Nutrient Recovery Technologies for Farm-Based Anaerobic Digesters . . . ". Washington State University. Nov. 6, 2013. 41 Pages.

A. A. Szogi, et al. "Phosphorus Recovery from Poultry Litter". vol. 51(5). American Society of Agricultural and Biological Engineers. 2008. pp. 1727-1734.

* cited by examiner

US 10,384,982 B2

WASTE MATERIAL PROCESSING SYSTEM

CROSS-REFERENCE TO RELATED APPLICATIONS

This non-provisional U.S. patent application claims priority under 35 U.S.C. § 120 to U.S. Patent Application No. 62/215,859, filed on Sep. 9, 2015. The entire content of U.S. Patent Application No. 62/215,859 is hereby incorporated herein by reference in its entirety.

BACKGROUND

Field of the Invention

The present invention generally relates to a process and system for treating organic waste materials. More specifically, the present invention relates to a process and system for treating waste materials that captures hydrocarbon gases and produces salable organic material and nutrient enhanced media in at least two distinct particle size fractions while recycling a reduced salinity water back into the system.

Background Information

Organic waste products such as chicken waste materials include high levels of nutrients, including salts and metals.

SUMMARY

One object is to process organic waste material and produce useful products therefrom.

In view of the state of the known technology, one aspect of the present disclosure is to provide an organic waste material processing system with a pretreatment section, a waste processing section, a hydrocarbon vapor processing section, an electric power producing apparatus and a waste post-processing section. The pretreatment section includes a waste material holding tank and a slurry-producing device configured to process organic waste material into a slurry. The waste processing section has a first waste processing part having at least one pressurizeable tank connected to the pretreatment section receiving slurry therefrom, a slurry temperature adjusting part and a first hydrocarbon capturing structure configured to capture hydrocarbon vapors produced by the slurry within the at least one pressurizeable tank at a predetermined temperature. The hydrocarbon vapor processing section is configured to collect captured hydrocarbon vapors from the waste processing section. The electric power producing apparatus is connected to the hydrocarbon vapor processing section and is configured to generate electricity using hydrocarbon vapor from the hydrocarbon vapor processing section. The electric power producing apparatus provides electric power to at least the pretreatment section and the waste processing section. The waste post-processing section is connected to the waste processing section and is configured to receive processed slurry therefrom. The waste post-processing section is configured to produce salable organic materials, nutrient enhanced media and recycled water that is fed to the pretreatment section.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

A description is provided below of a waste processing system 10. Thereafter, a description is provided for one combination of processes performed to process organic waste materials $M_O$ using the waste processing system 10. Thereafter, a description of salable materials 22 produced from the processed organic waste material $M_O$ is provided.

Figure 1:
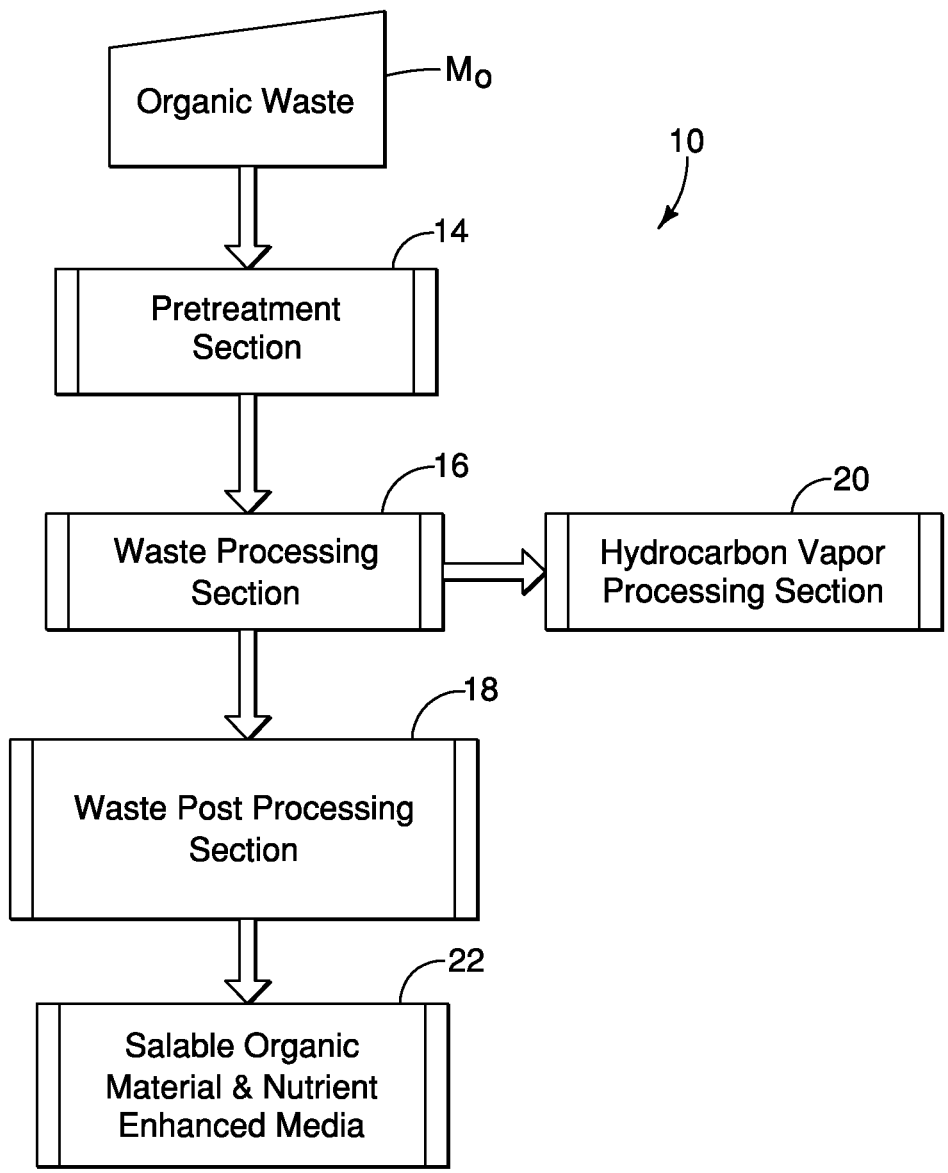
FIG. 1 is an overall schematic view of an organic waste material processing system that includes a pretreatment section, a waste processing section, a waste post-processing section, and a hydrocarbon vapor processing section in accordance with a first embodiment.

Referring initially to FIG. 1, a schematic block diagram showing portions of the waste processing system 10 for processing the organic waste materials $M_O$, is illustrated in accordance with a first embodiment.

The waste processing system 10 is a flexible system that can be used to process a variety of materials using a variety of processes. However, in the description below, one example of many possible combinations of processes that can be conducted by the waste processing system 10 is described. This combinations of processes described herein below make use of the waste processing system 10 to process and transform the organic waste materials $M_O$ into the salable materials 22. It should be understood from the drawings and the description herein that the waste processing system 10 can be used to conduct any of a variety of combination of processing steps and operations, and is not limited to usage with the combination of processes described herein below.

As used herein below, the term "organic waste materials $M_O$" can include any of a variety of materials. However, for purposes of understanding the invention, the organic waste materials $M_O$ described below can be solid poultry or animal wastes including any materials containing a mixture of poultry or animal urine, feces, undigested feed, and optionally bedding material. Additionally, the organic waste materials $M_O$ can include: different types of poultry manure such as litter (manure mixed with bedding material) or cake (manure with minimal bedding material); and/or different types of animal wastes such as manure mixed with bedding materials (such as in deep bedding systems for pig or cow rearing) or animal wastes with minimal bedding material (such as scraped or centrifuged manure or manure collected with belt systems); and or different types of organic materials such as food waste, agricultural waste, or industrial waste.

As shown in FIG. 1, the waste material processing system 10 includes a pretreatment section 14, a waste processing section 16, a waste post processing section 18 and a hydrocarbon vapor processing section 20, which can be configured to produce the salable organic materials and nutrient enhanced media (salable materials 22), as described in greater detail below.

Figure 2:
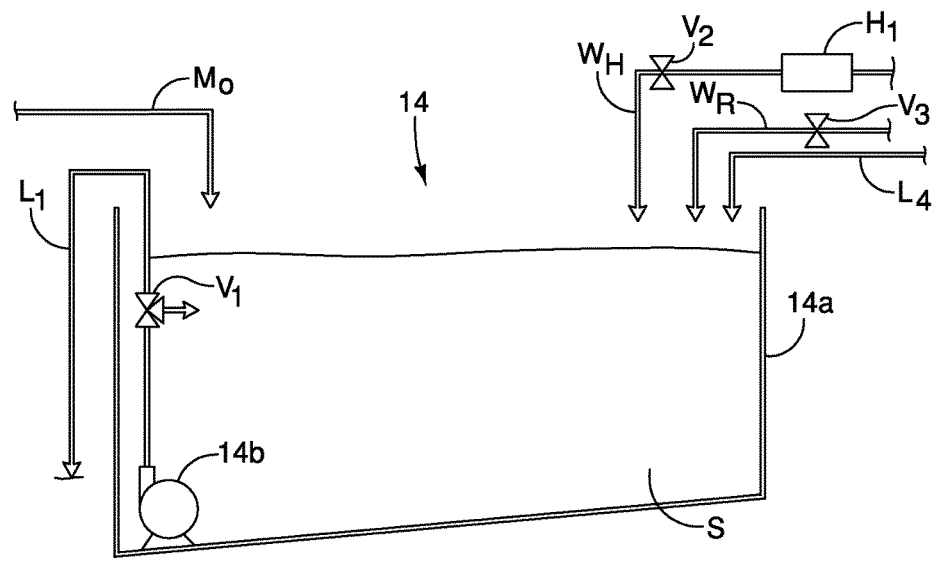
FIG. 2 is a schematic diagram showing a first part of the pretreatment section including a holding tank and a grinding device that produces a slurry in accordance with the first embodiment.
Figure 3:
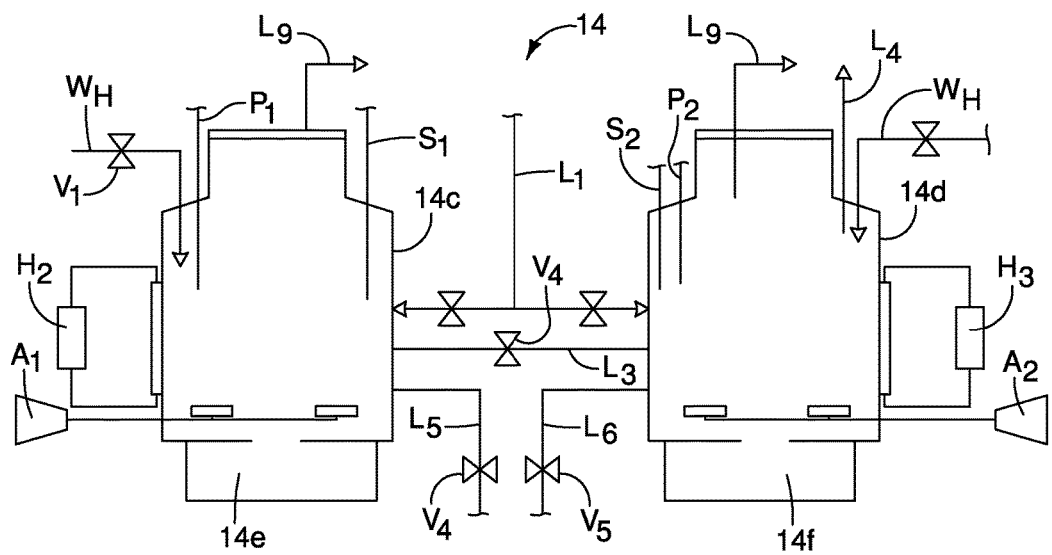
FIG. 3 is a schematic view of second part of the pretreatment section including a pair of pressurize-able tanks with heat adjusting portions and pH measuring sensors that conduct a first phase of anaerobic digestion in accordance with the first embodiment.

FIGS. 2 and 3 show parts of the pretreatment section 14. Specifically, FIG. 2 shows a first part of the pretreatment section 14 that includes a pretreatment tank 14a and a particle size homogenization mechanism 14b. The organic waste materials $M_O$ is fed into the pretreatment tank 14a via any of a variety of mechanisms. For example, a hopper (not shown) can provide the organic waste materials $M_O$ to the pretreatment tank 14a, or delivery vehicles such as truck or tankers can directly feed the organic waste materials $M_O$ into the pretreatment tank 14a. The particle size homogenization mechanism 14b can be any of a variety of pump/grinding mechanisms configured to reduce the overall size of the organic waste materials $M_O$ by, for example, grinding, crushing and/or pulverizing the organic waste materials $M_O$ thereby reducing the size of particle of compositions that make up the organic waste materials $M_O$. The particle size homogenization mechanism 14b can include a pump (not shown) that further moves and/or pumps the organic waste materials $M_O$ such that the organic waste materials $M_O$ is circulated around the pretreatment tank 14a. Hence, the organic waste materials $M_O$ circulates through the pretreatment tank 14a via pumping and grinding action of the particle size homogenization mechanism 14b. Since grinding and pulverizing mechanisms are conventional mechanical devices, further description is omitted for the sake of brevity.

The pretreatment tank 14a is provided with a hot water feed $W_H$ and a recycled water feed $W_R$ that may be one and the same. While the particle size homogenization mechanism 14b homogenizes the organic waste materials $M_O$ thereby turning it into the slurry S, water is added to provide workability and flowability to the slurry S, as well as to aid in the various downstream processing. In other words, while the organic waste materials $M_O$ are being reduced in size by the particle size homogenization mechanism 14b to a desired size, a slurry S is formed with the added water. A valve $V_1$ can be operated to change the flow of the slurry S from recirculation within the pretreatment tank 14a to a releasing operation in which the slurry S is pumped via a conduit $L_1$ to the next portion of the pretreatment section 14, as described further below.

The hot water feed $W_H$ is a device that can raise and/or adjust the temperature of the organic waste materials $M_O$ (and the subsequently produced slurry S) in the pretreatment tank 14a and dilute the organic waste materials $M_O$. Water passing to the hot water feed $W_H$ is heated by a heater $H_1$ that can be a dedicated heater or can be a water heater that heats water provided to the various portions of the water processing system 10, as described further below. Flow of hot water through the hot water feed $W_H$ is controlled via a second valve $V_2$. As is explained in greater detail below in a description of a first embodiment of an organic waste treatment process, the slurry S is further processed by the downstream portions of the waste material processing system 10. The hot water feed $W_H$ can be provided with municipal water that is heated by the heater $H_1$ or can be supplied with recycled water that is also heated by the heater $H_1$.

In order to provide further control of the temperature and dilution of the slurry S produced within the pretreatment tank 14a, a separate water source can also be provided. Specifically, the recycled water feed $W_R$ can provide additional heated or unheated water fed directly into the pretreatment tank 14. The recycled water feed $W_R$ is controlled via a third valve $V_3$. The source and production of the recycled water provided to the hot water feed $W_H$ and the recycled water feed $W_R$ is described in greater detail below.

As an alternative to the heater $H_1$, it is possible to provide the pretreatment tank 14a with a separate, independent heating system such as a water jacket or manifold (not shown) that surrounds the pretreatment tank 14a. The water jacket or manifold can be provided with a temperature controlled fluid that heats and/or cools the pretreatment tank 14a in order to achieve a desired temperature for the slurry S being produced within the pretreatment tank 14a from the organic waste materials $M_O$.

FIG. 3 shows a second part of the pretreatment section 14. The second part of the pretreatment section 14 includes a pair of preparation tanks 14c and 14d. Each of the preparation tanks 14c and 14d includes fluid manifolds that surround each of the tanks 14c and 14d, with heat control systems $H_2$ and $H_3$ pumping temperature-controlled fluids to the manifolds. The heat control systems $H_2$ and $H_3$ can be provided with dedicated heat sources or can be provided with heat via the heater $H_1$. Alternatively, the heater $H_1$ and the heater control systems $H_2$ and $H_3$ can all be provided with heat from a single central heating device configured to service the entire waste processing system 10. Further, the heat control systems $H_2$ and $H_3$ can include refrigeration portions such that the heat control systems $H_2$ and $H_3$ provide heating and/or cooling the slurry S thereby providing control for bringing and maintaining the slurry S therein at a predetermined temperature or within a predetermined temperature range. The preparation tanks 14c and 14d are pressurizeable with upper portions thereof defining hydrocarbon capturing structures connected to conduits $L_9$ which collect hydrocarbon vapors captured within the tanks 14c and 14d, as described in greater detail below. Each of the preparation tanks 14c and 14d further includes aeration devices $A_1$ and $A_2$ that are configured to provide air to the interior of each of the preparation tanks 14c and 14d. Each of the tanks 14c and 14d includes respective pH sensors $S_1$ and $S_2$, and reagent delivery mechanism $P_1$ and $P_2$. The reagent delivery mechanisms $P_1$ and $P_2$ can each be connected to both acidic and alkaline reagents for adjusting pH of the slurry S, if necessary. The reagent delivery mechanism $P_1$ and $P_2$ can also be connected to tanks (not shown) configured to retain alternative materials and/or reagents necessary for operating the waste processing system 10.

The slurry S is fed to each of the preparation tanks 14c and 14d by the first conduit $L_1$ from the pretreatment tank 14a. The preparation tanks 14c and 14d are connected to one another via a conduit $L_3$ allowing flow of the slurry S therebetween, if necessary or desired. A valve $V_4$ can be included in the conduit $L_3$ to open or block flow through the conduit $L_3$. An overflow conduit $L_4$ can optionally be provided to one or both of the preparation tanks 14c and 14d. In FIG. 3, only the preparation tank 14d is shown with the overflow conduit $L_4$, which directs overflow slurry S back to the pretreatment tank 14a, as shown in FIG. 2. However, it should be understood from the drawings and the description herein that both of the preparation tanks 14c and 14d can be provided with overflow conduits $L_4$.

In the preparation tanks 14c and 14d, the slurry S can be, for example, aerated, heated, cooled and/or undergo pH adjustments to achieve desired overall conditions of the slurry S, depending upon the combination of processes being employed. However, it is not necessary to utilize all of these capabilities of the preparation tanks 14c and 14d. Rather, the preparation tanks 14c and 14d are provided with the heat control systems $H_2$ and $H_3$, the aeration devices $A_1$ and $A_2$, the pH sensors $S_1$ and $S_2$, and the reagent delivery mechanism $P_1$ and $P_2$ in order to allow flexible overall usage of the preparation tanks 14c and 14d and the waste processing system 10. After all desired processing within the preparation tanks 14c and 14d has at least partially been accomplished, the conduits $L_5$ and $L_6$ and flow control valves $V_5$ and $V_6$ are provided to provide selective flow out of the preparation tanks 14c and 14d to the further downstream portions of the waste processing system 10. A pump (not shown) can be provided to draw the slurry S from the preparation tanks 14c and 14d through the conduits $L_5$ and $L_6$ for further downstream processing. Further, each of the tanks 14c and 14d includes a respective clean out section 14e and 14f used to routinely collect debris and clean out such debris.

Figure 4:
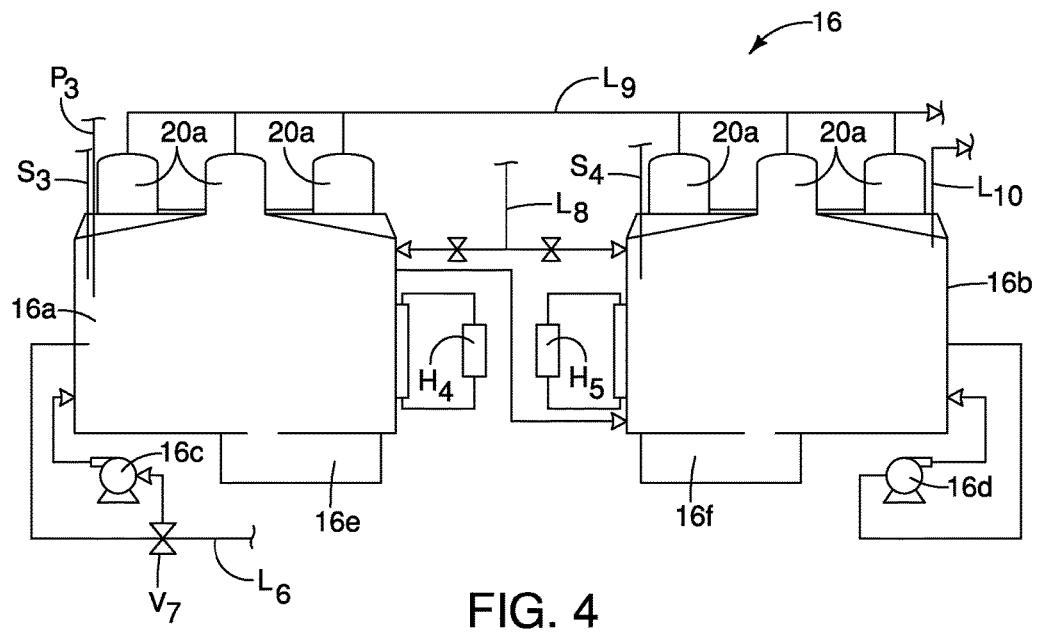
FIG. 4 is a schematic view of a first part of the waste processing section including a pair of anaerobic digesting tanks that each include a heat adjusting portion, a pH adjusting portion and hydrocarbon capturing portions in accordance with the first embodiment.

FIG. 4 shows a first part of the waste processing section 16, including pressurize-able digestion tanks 16a and 16b that receive the slurry S from the pretreatment tanks 14c and 14d via the conduit $L_6$. Each of the tanks 16a and 16b includes respective heat regulating systems $H_4$ and $H_5$ for heating and/or cooling the slurry S in order to bring the slurry S to, and maintain the slurry S at a desired predetermined temperature or within a predetermined temperature range. The heat regulating system $H_4$ and $H_5$ can be supplied with stand-alone heating and cooling devices, or can be connected to a central heating device and a central cooling device that supplies temperature regulating fluids to each of the various tanks as needed or desired. Each of the tanks 16a and 16b includes a respective pH sensor $S_3$ and $S_4$ and respective reagent delivery mechanisms $P_3$ and $P_4$ that are supplied with acid and/or alkaline materials as needed, and are configured to deliver such materials to the tanks 16a and 16b in response to determining the need for a pH adjustment. The reagent delivery mechanisms $P_3$ and $P_4$ can also be connected to tanks (not shown) configured to retain bacteria, alternative materials and/or reagents necessary for operating the waste processing system 10. Since pH sensors and reagent delivery mechanisms, such as the respective reagent delivery mechanisms $P_1$, $P_2$, $P_3$ and $P_4$ are conventional mechanisms, further description is omitted for the sake of brevity.

The tank 16a is provided with slurry S from the conduit $L_6$ via a valve $V_7$ and pump 16c. The pump 16c is connected to the tank 16a such that with the valve $V_7$ in a first setting, the pump 16c can recirculate the slurry S out of and back into the tank 16a. In a second setting, the valve $V_7$ is set so that the pump 16c draws the slurry S from the conduit $L_6$ and into the tank 16a. A conduit $L_7$ connects an upper portion of the tank 16a to the tank 16b such that slurry S can move from the tank 16a to the tank 16b.

The tanks 16a and 16b are further provided with a water source via conduit $L_8$. The conduit $L_8$ can be provided with recycled water, fresh water or brine that can be unheated or heated. The tank 16b includes a pump 16d that is connected to the tank 16b such that with the pump 16d can recirculate the slurry S out of and back into the tank 16b.

On an upper surface of each of the digestion tanks 16a and 16b there are a plurality of hydrocarbon vapor capturing structures 20a that are also pressurize-able. The hydrocarbon vapor capturing structures 20a are open to, or are in fluid communication with the interior of respective ones of the tanks 16a and 16b. The water and/or brine introduced via the conduit $L_8$ can be configured to provide and build up hydrostatic pressure within the tanks 16a and 16b, as well as in the plurality of hydrocarbon vapor capturing structures 20a. The hydrocarbon vapor capturing structures 20a are configured to capture hydrocarbon vapors (gases) released form the slurry S, and deliver the captured vapors to the hydrocarbon vapor processing section 20, as is described in greater detail below. The hydrocarbon vapor capturing structures 20a are connected to conduits $L_9$ that direct collected vapors to the hydrocarbon vapor processing section 20. Each of the digestion tanks 16a and 16b can also include clean out portals 16e and 16f that are provided for receiving precipitated material for subsequent removal. The clean-out portals 16e and 16f are configured to with a door (not shown) that moves between a closed orientation sealing the clean-out portals from an interior of the corresponding one of the tanks 16a and 16b and an open orientation allowing flow between the tanks 16a and 16b. When in the closed orientation, the clean-out portal can be cleaned without interfering with operation of the waste processing system 10.

The tank 16b is also provided with a conduit $L_{10}$ that is configured to release processed slurry S for further downstream processing, as described further below.

Figure 5:
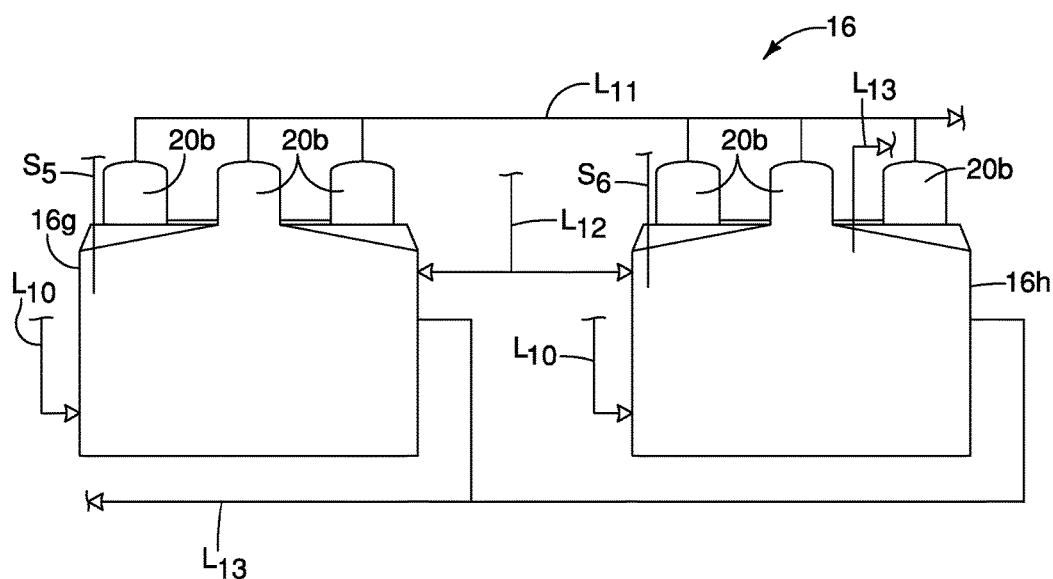
FIG. 5 is schematic view of a second part of the waste processing section including effluent storage tanks that also include additional hydrocarbon vapor capturing devices in accordance with the first embodiment.

FIG. 5 shows a second part of the waste processing section 16. There are two effluent storage tanks 16g and 16h. The tanks 16g and 16h both receive the digested slurry S from the pressurize-able digestion tank 16b via the conduit $L_{10}$. The effluent storage tanks 16g and 16h also include additional hydrocarbon vapor capturing structures 20b that capture hydrocarbon vapors released from the slurry S in a manner similar to the hydrocarbon vapor capturing structures 20a and feed the captured vapors the hydrocarbon vapor processing section 20 via conduit $L_{11}$. Each of the tanks 16g and 16h includes a water feed via conduit $L_{12}$. The conduit $L_{12}$ can be provided with recycled water, fresh water or brine that is unheated or, alternatively, can be heated and can be configured to provide and build up hydrostatic pressure within the tanks 16a and 16b, as well as in the plurality of hydrocarbon vapor capturing structures 20a and 20b.

Each of the tanks 16g and 16h can include a pH sensor $S_5$ and $S_6$ and well as reagent delivery mechanisms $P_5$ and $P_6$ that are supplied with acid and/or alkaline materials as needed, and are configured to deliver such materials to the tanks 16g and 16h in response to determining the need for a pH adjustment. Processed slurry S leaves the tanks 16g and 16h via conduits $L_{13}$.

Figure 6:
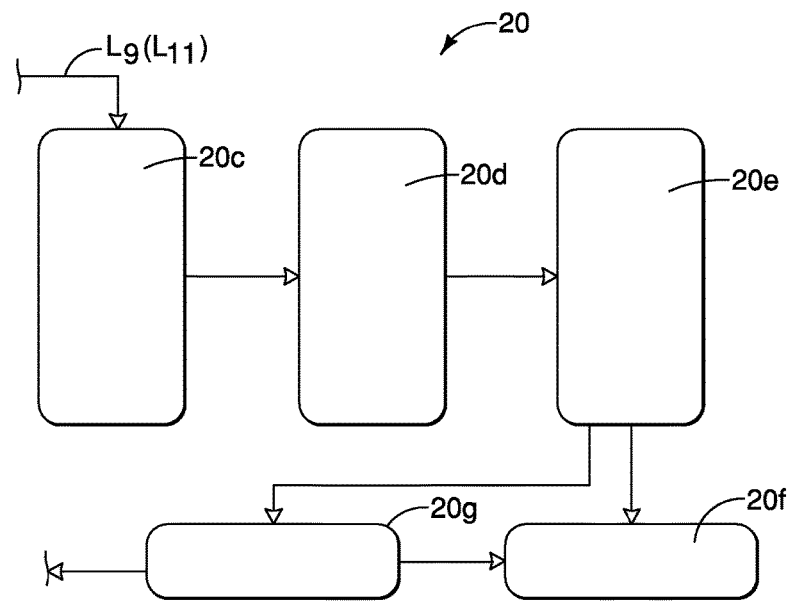
FIG. 6 is a block diagram that schematically depicts the hydrocarbon vapor processing section showing a hydrostatic pressurization section, a desulfurization section, a desiccation section, an energy production section and a connection to an external power section for disposal of excess energy produced by the hydrocarbon vapor processing section in accordance with the first embodiment.

A description of the hydrocarbon vapor processing section 20 is now provided with specific reference to FIG. 6. The hydrocarbon vapor processing section 20 includes a hydrocarbon capturing part 20c, a hydrocarbon vapor treatment part 20d and an energy production part 20e. The hydrocarbon capturing part 20c receives captured hydrocarbon vapors from tanks 14a and 14b, the hydrocarbon vapor capturing structures 20a and the hydrocarbon vapor capturing structures 20b of the tanks 16a, 16b, 16g and 16h of the waste processing section 16 via the conduits $L_9$ and $L_{11}$. The hydrocarbon capturing part 20c can include a pump (not shown) or compressor (not shown) and storage tanks (not shown) that are configured to store pressurized gases in a conventional manner. The hydrocarbon vapor treatment part 20d can include any of a variety of vapor preparing features, such as a desulfurization apparatus and a moisture removing apparatus (desiccation). The hydrocarbon vapor treatment part 20d can also include a compressor (not shown) and storage tanks (not shown) for storing processed hydrocarbon vapors. The energy production part 20e can be an electric generator (not shown) that is fueled by the processed hydrocarbon vapors prepared by the hydrocarbon vapor treatment part 20d. Power produced by the energy production part 20e is used to at least partially power the electrical equipment 20f of the waste processing system 10, such as pumps, heaters, valves, and other electrically powered portions of the waste processing system 10. If excess electricity is produced by the energy production part 20e, it can be provided as external power 20g to a local electric grid. Conversely, if the electricity produced by the energy production part 20e is not sufficient to power the electrically powered equipment 20f of the waste processing system 10, external power 20g from a local electric grid can be used to power a portion of the waste processing system 10.

Figure 7:
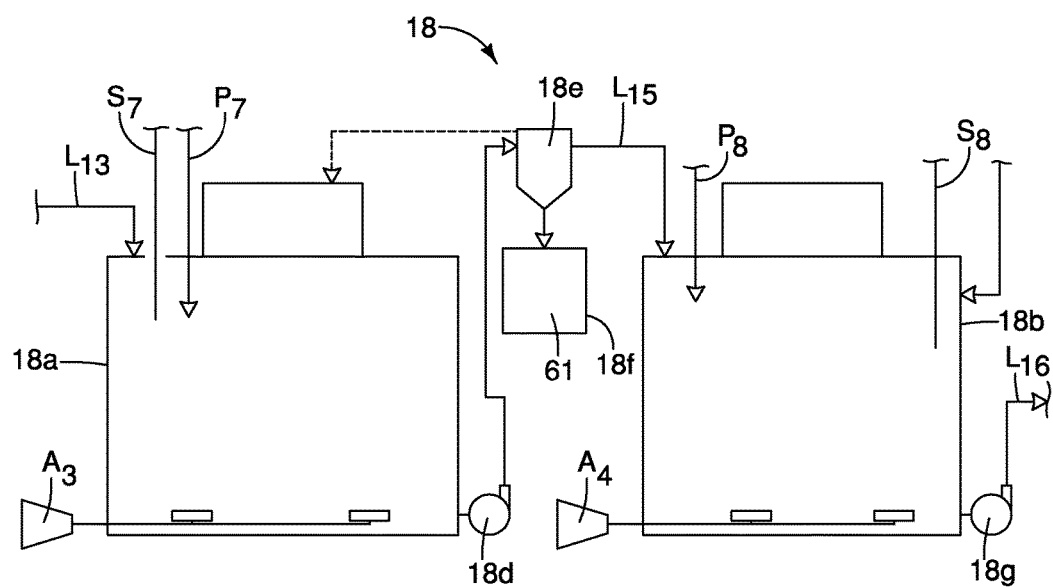
FIG. 7 is a schematic diagram showing a first portion of the waste post-processing section including acid wash tanks and a first solid separator, the acid wash tanks being configured to adjust the pH of the slurry, the solid separator being configured to extract salable organic material and nutrient enhanced media from the processed slurry in accordance with the first embodiment.
Figure 8:
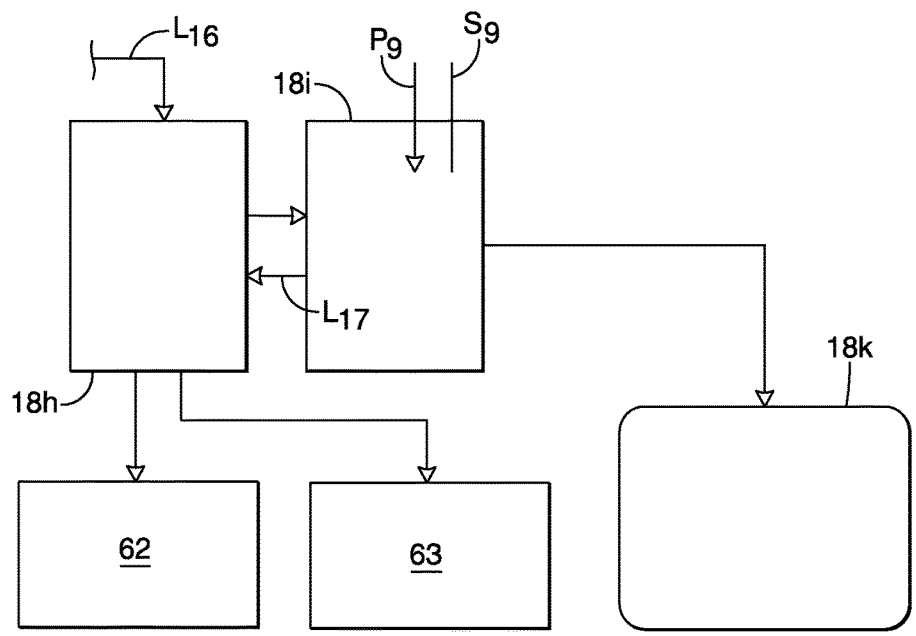
FIG. 8 is a schematic diagram showing a second portion of the waste post-processing section including a second solid separator, a filter membrane, a recycled water collection vessel, and salable products produced by the system in accordance with the first embodiment.

A description of the waste post processing section 18 is now provided with specific reference to FIGS. 7 and 8. A first part of the waste post processing section 18 is shown in FIG. 7. The first part of the waste post processing section 18 includes acidification tanks 18a and 18b that define a first pH adjusting section. The tank 18a receives processed slurry S from the tanks 16g and 16h via the conduit $L_{13}$. The tank 18a includes a pH sensor $S_7$, a reagent delivery mechanism $P_7$, an aeration or mixing device $A_3$ and an outlet that is optionally connected to a pump 18d. The pH sensor $S_7$ is provided to detect the current pH of the processed slurry S. The reagent delivery mechanism $P_7$ can include a pH adjusting mechanism that is configured to selectively add either acidic material(s) and/or alkaline material(s) in order to adjust to the current pH of the slurry in the tank 18a and bring it to a desired pH level or within a predetermined pH range. The reagent delivery mechanism $P_7$ can also be connected to additional reagent delivery devices, such as an anti-foaming agent delivery device. The aeration device $A_3$ is provided to aerate the slurry S in the tank 18a, if necessary. The pump 18d is connected to a conduit L14 that feeds the slurry S into a first solid separation device 18e.

The first solid separation device 18e is configured to separate solid portions and liquid portions of the processed slurry S. The first solid separation device 18e can be, for example, a centrifuge device. However, the first solid separation device 18e can be sieves, gravity screens, centrifuges, auger presses, or other dewatering devices. The solid portions separated from the processed slurry S by the first solid separation device 18e are fed into a hopper $S_8$ and define stable organic material 61 that is described in greater detail below with reference to Table 1. The remaining liquid portions of the processed slurry S are fed via conduit $L_{15}$ to the tank 18b where they are stored until fed via a pump 18g via line $L_{16}$ to downstream portions of the waste processing system 10. Since solid separation devices such as the first solid separation device 18e are conventional devices, further description is omitted for the sake of brevity.

The tank 18b provided with the processed slurry S from the first solid separation device 18e via the conduit $L_{15}$. The tank 18b includes a pH sensor $S_8$, a reagent delivery mechanism $P_8$, an aeration device $A_4$, a conduit $L_{16}$ that serves as a water feed (if necessary) and an outlet connected to a pump 18g. The pH sensor $S_8$ is provided to detect the current pH of the processed slurry S. The reagent delivery mechanism $P_8$ can include a pH adjusting mechanism configured to selectively add either an acidic material and/or an alkaline materials in order to adjust to the current pH of the slurry in the tank 18b and bring it to a desired pH level or within a predetermined pH range. The reagent delivery mechanism $P_8$ can also be connected to additional reagent delivery devices.

The aeration device $A_4$ is provided to aerate the slurry S in the tank 18b, if necessary. The pump 18g is connected to a conduit $L_{17}$ that feeds the slurry S to the second part of the waste post processing section 18, as described further below.

The second part of the waste post processing section 18 is shown in FIG. 8 and includes a second solid separation section 18h, a pH adjusting section 18i and an optional water filtration section 18k. The second solid separation section 18h can include a dewatering apparatus such as a dewatering skid or other similar device that can extract predetermined materials from the processed slurry S, thereby producing a salable organic product 62 and a nutrient enhanced media 63 (in separate operations), as discussed in greater detail below with respect to Table 1.

The second pH adjusting section 18i can include a tank and/or a reactor provided with a pH sensor $S_9$ and a reagent delivery mechanism $P_9$. The reagent delivery mechanism $P_9$ can include a pH adjusting mechanism configured to selectively add either acidic material(s) and/or alkaline material(s) in order to adjust to the current pH of the slurry S bring it to a desired pH level or within a predetermined pH range. The reagent delivery mechanism $P_9$ can also be connected to additional reagent delivery devices, such as specific reagent delivery devices. The solid portions separated from the processed slurry S by the second solid separation section 18h in a second solid separation process are fed into a hopper $S_8$ and define the salable organic product 62 that is described in greater detail below with reference to Table 1.

The processed slurry S can optionally be recirculated back to the second solid separation section 18h if necessary via the conduit $L_{17}$, for further liquid/solid separation in a third solid separation process. The solid portions separated from the processed slurry S by the second solid separation section 18h in the third solid separation process define the nutrient enhanced media 63 that is described in greater detail below with reference to Table 1. Thereafter, remaining filtrate from either the second or third solid separation processes can be fed to the optional water filtration section 18k, which can include, for example, a reverse osmosis apparatus (a filtration section that includes membrane filtration). Alternatively, the optional water filtration section 18k can be replaced with sieves, gravity screens, centrifuges, auger presses, or other dewatering devices. The water filtration section 18k can further include various water tanks (not shown) for storing the filtered water produced by the water filtration section 18k. The water produced by the water filtration section 18k produces water that is referred to above as recycled water to the various portions of the waste processing system 10, including the pretreatment section 14. Solids from the water filtration section 18k can also define the nutrient enhanced media 63, as discussed in greater detail below with respect to Table 1. Since membrane filtration systems, such as reverse osmosis apparatus, and water storage structures are conventional features, further description is omitted for the sake of brevity.

Figure 9:
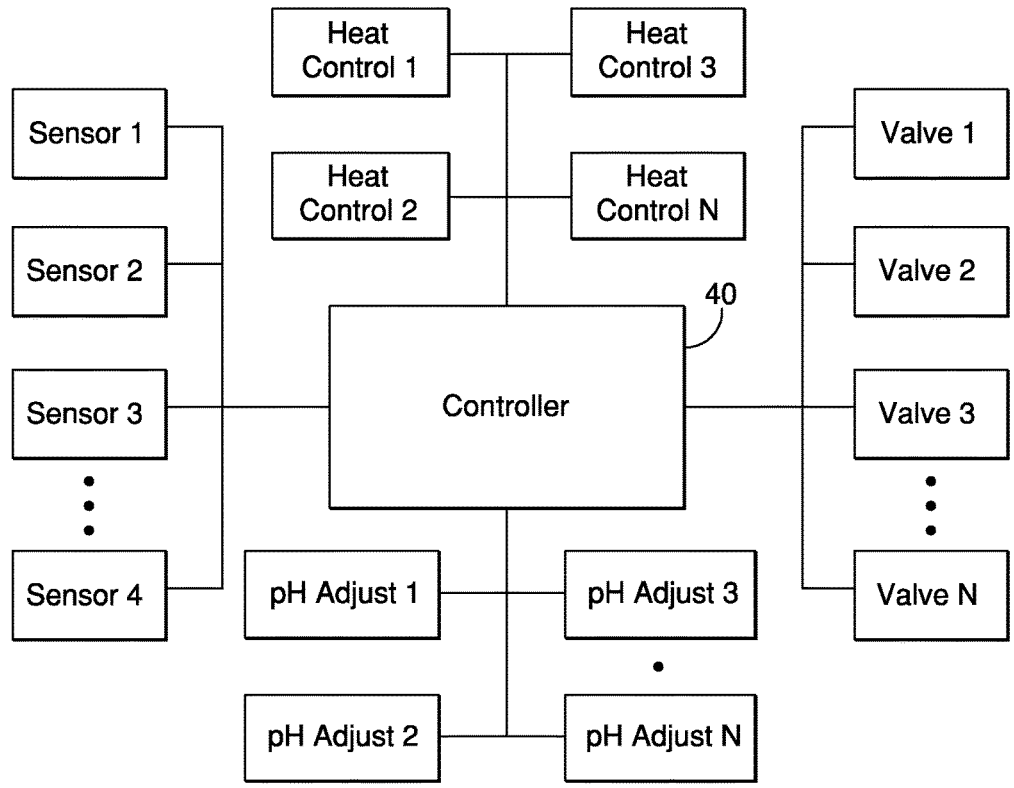
FIG. 9 is a schematic block diagram showing a controller connected to various sensors, valves, temperature controllers and control mechanisms of the organic waste material processing system in accordance with the first embodiment.

A description is now provided of a control system that monitors the various sensors and controls the various valves, and feeds of the waste processing system 10. As shown in FIG. 9, a controller 40 is connected to all of the electronically controlled elements of the waste processing system 10, such as the pH sensor $S_1$ through $S_N$, the mechanism $P_1$ through $P_N$ (and their corresponding reagent, acid and alkaline feed controls), the temperatures controls for the heater $H_1$ through $H_N$ and each of the valves $V_1$ through $V_N$. Although not shown in the drawings, each of the tanks 14a, 14b, 14c, 14d, 16a, 16b, 18a and 18b can include a corresponding temperature sensor (not shown) that are all connected to the controller 40. Thus, the controller 40 is connected to the various elements of the waste processing system 10 and is programmed to operate the waste processing system 10 to carry out any of a variety of combination of processes.

Basic Process Steps

The organic waste treatment processing system 10 performs the various steps outlined below.

First, in a pretreatment process, the waste materials $M_O$ (organic matter, e.g. manure, food waste, crop waste), are optionally homogenized with the addition of water/recycled water with mechanisms such as grinders, shredders, hammermills and equipment obvious to those familiar in the art. In this pretreatment process water and/or recycled water is added to form a slurry S which may be subsequently temperature adjusted to a predetermined temperature or temperature range between 15° C. and 40° C. and/or further homogenized with equipment such as grinder pumps, grinders and similar engineered devices to form the slurry S.

Next, the slurry S resulting from the pretreatment process is treated in a waste treatment process that includes a first phase of anaerobic digestion (AD) and a second phase of anaerobic digestion (AD). The first phase of AD includes subjecting the slurry S to a predetermined air pressure and predetermined temperature using at least one pressurizeable tank or a plurality of tanks in which the organic waste slurry S undergoes microbially-facilitated hydrolysis and acidogenesis to produce hydrocarbon vapors and to condition the slurry for delivery to the second phase of AD. The second phase of AD include moving the slurry S into one or more pressurizeable and temperature adjustable tanks in which the slurry (the waste material) is biologically degraded at a predetermined temperature or temperature range to reduce total solids and odor and mineralize nutrients and metals in the slurry as a conditioning step for a subsequent waste post-processing process steps while producing hydrocarbon vapors that are captured in an hydrocarbon vapor capture process using a hydrocarbon vapor processing system.

The waste post-processing process includes a first pH adjustment step in which mineral acids such as $H_2SO_4$, HCl, or combinations of mineral and organic acids are added to the digested slurry material in an optionally pressurizeable and/or temperature adjusted tank or a plurality of such tanks until the pH is at or below 6.0 in order to reduce pathogens, solubilize nutrients and metals, and destroy reserve alkalinity in the slurry.

A subsequent step in the waste post-processing process includes a first solids separation process in which particulate matter inherent in the slurry S larger than about 0.5-1.5 mm is removed via sieves, gravity screens, centrifuges, auger presses, or other dewatering devices to produce a stable, dewatered organic material 61 (described further below) and a filtrate. Production of the filtrate effectively removes approximately 95% of the water/liquid from slurry S (and the dewatered organic material 61).

Another subsequent step in the waste post-processing process includes a second solids separation process, optionally facilitated by the addition of a filtration aid such as, for example, diatomaceous earth, in which the filtrate from the first solids separation process is further processed by removing particulate matter smaller than about 0.5-1.5 mm using a mechanical or membrane-based dewatering device to produce a salable organic product 62 and a second filtrate made up of approximately 95% of water removed from the salable organic product 62.

In yet another subsequent step in the waste post-processing process, a second pH adjustment process 54 in which the pH of the filtrate resulting from the second solids separation process is adjusted above pH 7 using a caustic chemical (NaOH, KOH, $Mg(OH)_2$, $NH_3$ or similar) in an optionally pressurizeable and/or temperature adjustable tank or plurality of such tanks to increase the nutrient content of the filtrate and colloidize the soluble nutrients in solution.

In an optional subsequent step in the waste post-processing process, a third solids separation process in which the colloidal material from the second pH adjustment process is removed using a mechanical or membrane-based dewatering device to produce a nutrient enhanced media 63 that is discussed further below, and a recyclable water that can be reintroduced into the organic waste treatment processing system 10.

Example of Specific Process Steps

In accordance with a first embodiment, a specific combination of processes conducted by the waste processing system 10 is now described with specific reference to FIGS. 10-13.

Figure 10:
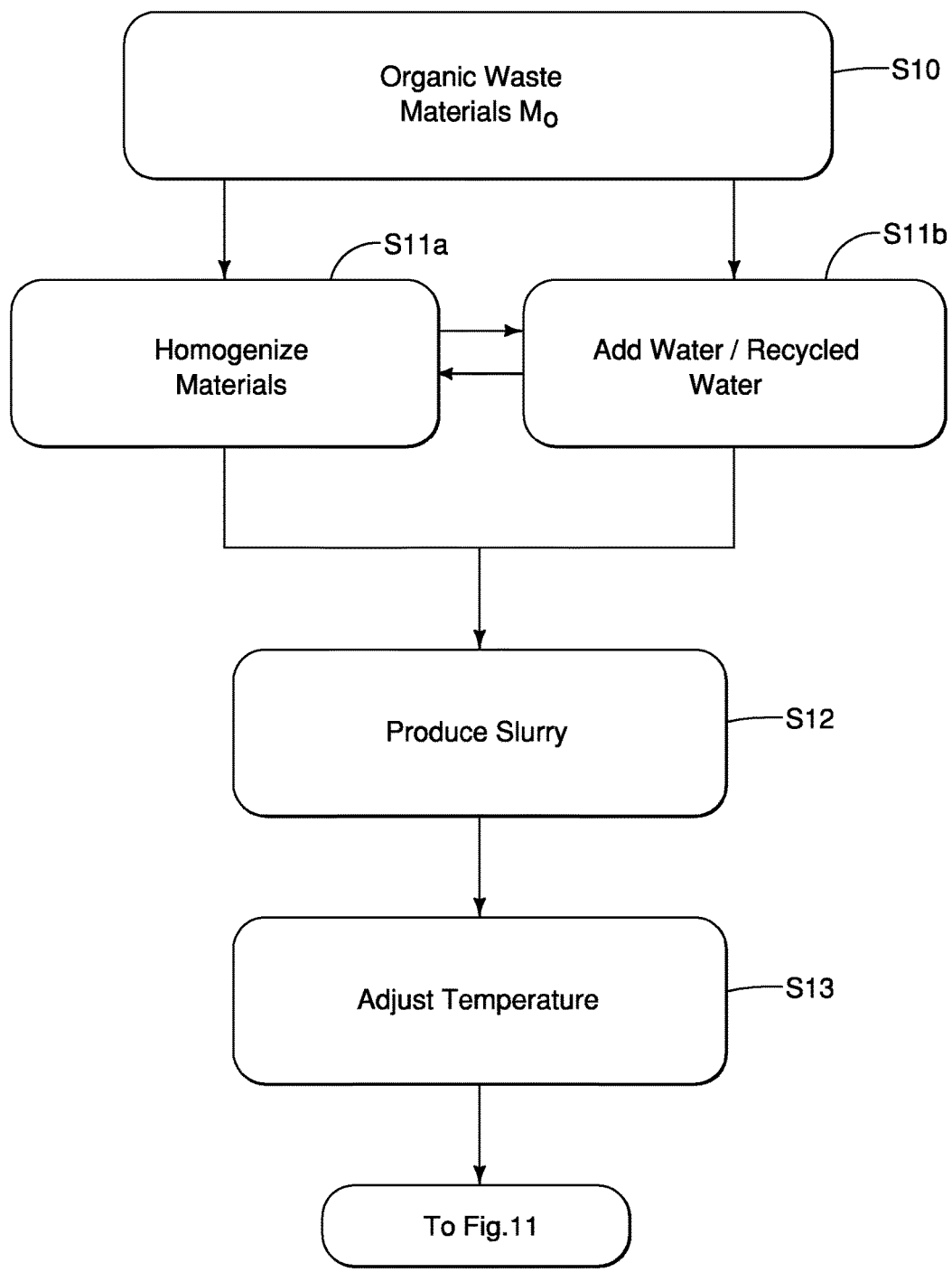
FIG. 10 is a flowchart showing basic steps of an organic waste treatment process performed by the organic waste material processing system, and in particular steps performed by the first part of the pretreatment section depicted in FIG. 2 including organic material grinding, diluting and slurry producing related operations in accordance with the first embodiment.

As shown in FIG. 10, an organic waste treatment process begins at step S10 with the delivery of organic waste materials $M_O$ to pretreatment tank 14a of the pretreatment section 14. As stated above, the organic waste materials $M_O$ can be delivered via a conveyor, a conduit, or delivered by vehicles delivering the organic waste materials $M_O$ to the pretreatment tank 14a. As shown at steps S11a and S11b, two inter-related operations can occur in either order (step S11a first, then step S11b or, step S11b followed by step S11a), or can occur simultaneously depending upon, for example, the condition of the organic waste materials $M_O$. Specifically, at step S11a, the organic waste materials $M_O$ the organic waste materials $M_O$ is pulverized, mashed or ground up by, for example, the particle size homogenization mechanism 14b. In step S11b, water is added to the pretreatment tank 14a in order to dilute and help liquefy and further homogenize the organic waste materials $M_O$ in the pretreatment tank 14a. The water added to the pretreatment tank 14a can be hot water, recycled water, brine, as well as mixtures thereof. Next at step S12, the organic waste materials $M_O$ continues to be mixed and pulverized, mashed or ground up by the particle size homogenization mechanism 14b and mixed with water such that the mixture of the water and the organic waste materials $M_O$ is pre-processed into the slurry S.

The addition of heated water at step S11b can begin a process of raising the overall temperature of the subsequently produced slurry S to a desired or predetermined temperature. The maximum particle size is variable depending upon the nature of the original organic waste material $M_O$. However, in the embodiments described herein, the maximum particle size within the slurry S can range from between 5 mm and 25 mm in overall diameter.

At step S13, the slurry S is pumped by, for example, the particle size homogenization mechanism 14b, which can include a pumping capability, or by a separate pump (not shown) from the tank 14a to the preparation tanks 14c and 14d (FIG. 3). In the tanks 14c and 14d, the homogenized slurry S undergoes temperature adjustment to predetermined temperature. In the embodiments described herein, the predetermined temperature can be between 15° C. and 40° C., but is more preferably between 25° C. and 35° C. At the bottom of FIG. 10, the flow of processes moves to the depictions in FIG. 11.

Figure 11:
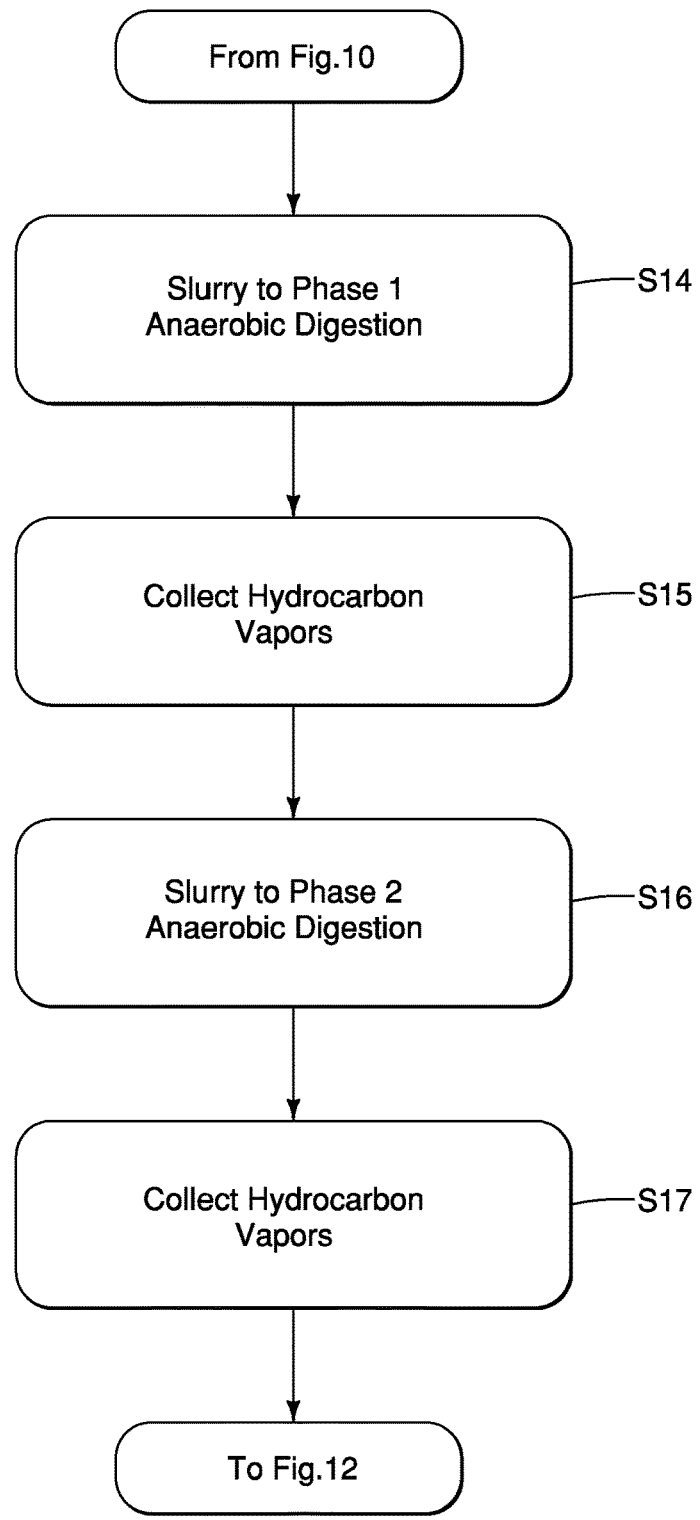
FIG. 11 is a second flowchart showing basic steps of the organic waste treatment process including steps performed by the waste processing section such as a first phase of anaerobic digestion and collection of hydrocarbon vapors performed using the pressurizeable tanks in FIG. 3 and the anaerobic digesting tanks depicted in FIG. 4, and a second phase of anaerobic digestion and additional collection of hydrocarbon vapors performed using the tanks depicted in FIG. 5 in accordance with the first embodiment.

As shown in FIG. 11, at step S14, the organic waste treatment process proceeds with a first phase of anaerobic digestion of the slurry S. Specifically, as the slurry S is heated within the tanks 14c and 14d, the slurry S is put into a state where microbial facilitated hydrolysis (anaerobic digestion) can begin, or the progress of such anaerobic digestion is initiated. At step S14, the heated slurry S within the tanks 14c and 14d is digested and hydrocarbon vapors begin to form, as indicated at step S15 in FIG. 11. The hydrocarbon vapors such as methane can initially be collected from the tanks 14c and 14d. Since the slurry S is heated within the tanks 14c and 14d, the first phase of anaerobic digestion of the slurry S continues in the tanks 14c and 14d. The anaerobic action within the tanks 14c and 14d can result in a decreased pH to between 6.0 and 8.0 pH, which can be monitored using the pH sensors $S_3$ and $S_4$. The anaerobic digestion results in the production and release from the slurry S of hydrocarbon vapors such as methane, which can initially be collected from the tanks 14c and 14d. However, as the anaerobic digestion of the slurry S continues, the heated slurry S is moved to the tanks 16a and 16b for further capture of the released hydrocarbon vapors and to move to a second phase of anaerobic digestion, as indicated at step S16 in FIG. 11.

Within the tanks 16a and 16b, the slurry S undergoes the second phase of anaerobic digestion (step S16), which can proceed naturally after an initial inoculation, since microbes and bacteria are present in the organic waste materials $M_O$. However, if the anaerobic digestion of the slurry S needs microbial or bacterial assistance in proceeding, various agents can be introduced into the slurry, such as *Streptococcus* sp., *Enterobacterium* sp., *Pseudomonas* sp., *Bacillus* sp., etc. Optionally, microbial organisms as mentioned above can be introduced along with optional micronutrients and elements such as B, Ni, Co, or pH adjusting chemicals such as $Ca(CO_3)_2$, $NaCO_3$.

At step S17 in FIG. 11, hydrocarbon vapors are collected in the tanks 16a and 16b via the hydrocarbon vapor capturing structures 20a. During the second phase of anaerobic digestion within the tanks 16a and 16b, the pressure within the tanks 16a and 16b can have a gas pressure within a range of between 5 kpa to approximately 20 kpa. Since the tanks 16a and 16b are provided with the heat regulating system $H_4$ and $H_5$, the temperatures within the tanks 16a and 16b can be achieved and maintained at a predetermined temperature or within a predetermined temperature range of, for example, between 25° C. and 40° C. The anaerobic action within the tanks 16a and 16b can result in a further decreased pH, which can be monitored using the pH sensors $S_3$ and $S_4$. During the first and second phases of anaerobic digestion (steps S14 through S17), the hydrocarbon vapors captured by the hydrocarbon vapor capturing structures 20a and 20b are fed to the hydrocarbon vapor processing section 20, as is described in greater detail below. The hydrocarbon vapors produced in the anaerobic digestion mainly include methane gas, but can also include small amounts of more complex hydrocarbon gases, including ethane and propane.

As mentioned above, the microbial facilitated hydrolysis can proceed without addition of a bacterial agent, depending upon the nature of the organic waste 12. Specifically, organic waste 12, such as poultry or other animal related waste, naturally has various microbial agents in it. Therefore, the anaerobic digestion proceeds naturally, in particular, once the temperature of the slurry S has been raised to the above-mentioned predetermined temperature range. However, if an agent is needed, *Streptococcus* sp., *Enterobacterium* sp., *Pseudomonas* sp., *Bacillus* sp., etc. can be introduced. However, since this is a self-organized biological process only a small quantity of any bacterial agent need be introduced, if at all.

The second phase of anaerobic digestion proceeds within the pressurizeable tanks 16a and 16b. Specifically, at step S16, the slurry S is moved from the tanks 14c and 14d to the tanks 16a and 16b. The tanks 16a and 16a are pressurizeable up to approximately 20 kpa. The tanks 16a and 16b can also optionally include the heat regulating systems $H_4$ and $H_5$.

The second phase of anaerobic digestion facilitates anaerobic digestion of the organic waste material $M_O$ and also proceeds at the above mentioned predetermined temperature or temperature range of between 25-40° C., and more preferably between 35-40° C. The organic waste material $M_O$ in the partially digested slurry S can be further biologically degraded via the presence of or introduction of *Pseudomonas* sp., *Bacillus* sp., *Syntrophomonas* sp., *Syntrophobacter* sp., *Methanobacterium* sp., *Methanosarcina* sp., *Methanococcus* sp., *Methanobacterium* sp., etc. The further anaerobic digestion within the tanks 16a and 16b (step S16) reduces total solids in the slurry S, reduces odor and mineralizes nutrients and metals in the slurry S while producing additional hydrocarbon vapors that are captured by the hydrocarbon vapor capturing structure 20b (step S17 in FIG. 11). The captured hydrocarbon vapors are then processed by the hydrocarbon vapor processing section 20.

In steps S14 through S16 when the slurry S is moved into the tanks 14a and 14b, the slurry S preferably has a total solids content of 5-15% by weight and preferably approximately 10% by weight. Upon exiting the tanks 16a and 16b, the slurry S preferably has 2-12% by weight of solid material, and ideally approximately 6% by weight of solids. However, hydrocarbon vapors are released and captured in this portion of the process. It should be understood that the reduction in solids content during Steps S14 through S16 are the result of microbial degradation and the associated production of hydrocarbon vapors.

Figure 12:
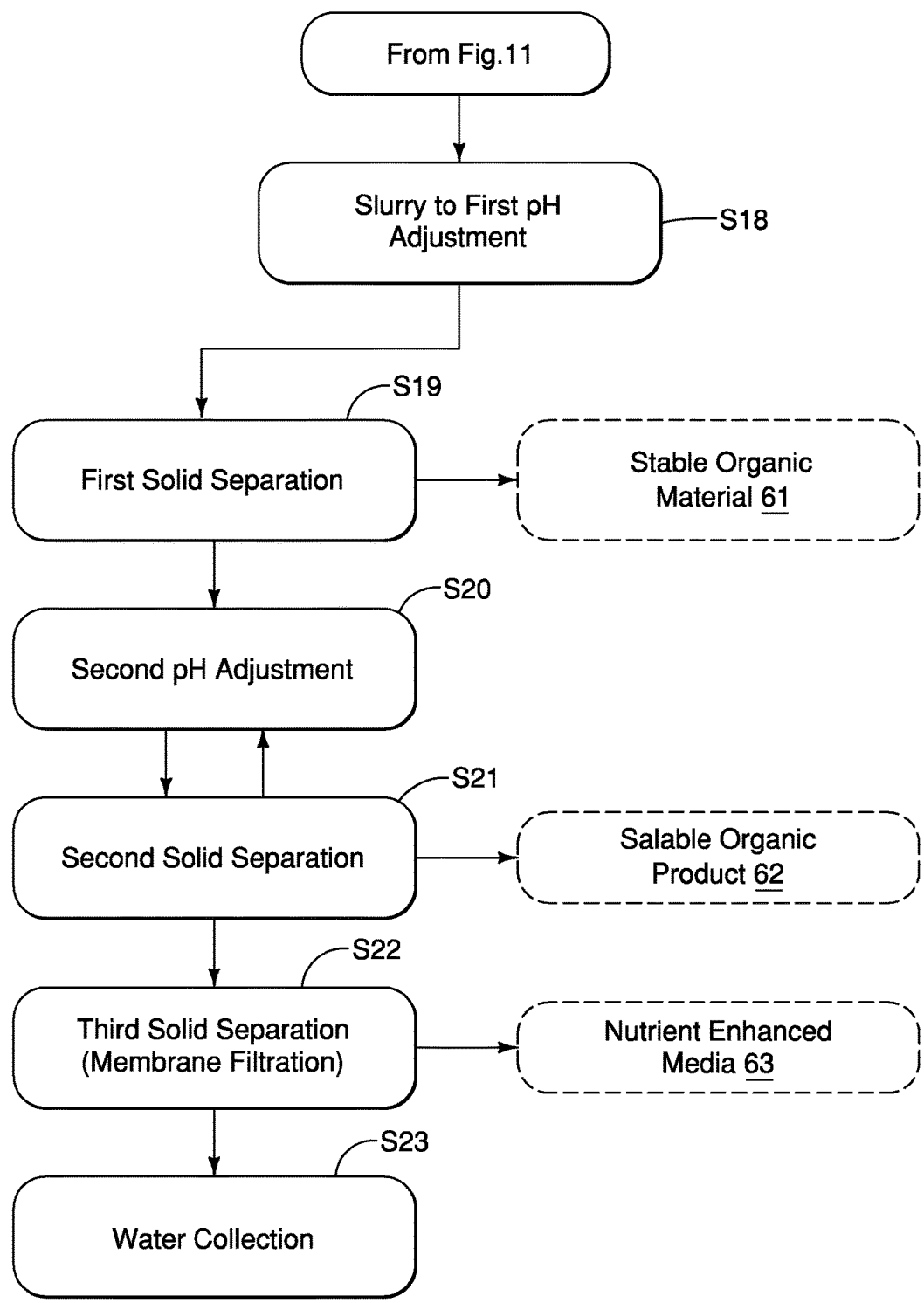
FIG. 12 is a third flowchart showing basic steps of the organic waste treatment process in accordance with the first embodiment.

As shown at the bottom of FIG. 11, the organic waste treatment process continues in the steps depicted in FIG. 12. After capturing further amounts of hydrocarbon vapors in step S17 in FIG. 11, the processed slurry S is moved to the waste post processing section 18 of the waste processing system 10. Specifically, the slurry S is moved to the effluent/acidification tanks 16g and 18a where it undergoes a first pH adjustment, as represented at step S18 in FIG. 12. At step S18, the processed slurry S is optionally heated and the tank 18a can be pressurized to between 0.0 kpa and 14.0 kpa (0.0-2.0 psi). Further, within the tank 18a, the pH of the processed slurry S is adjusted in the first pH adjustment step to a pH of between 3.5 and 4.5.

At step S19, after the processed slurry S has undergone the first pH adjustment, the slurry S is moved to the first solids separation device 18e (for example, a centrifuge) where a solid portion of the slurry S is separated from a liquid filtrate portion of the slurry S to produce a coarse but stable reduced-pathogen organic material 61 in a first solids separation process. The organic material 61 is described in greater detail below with reference to Table 1.

The first solids separation device 18e removes particles larger than about 0.5 mm to 1.5 mm from the slurry S and allows all particles smaller than about 0.5 mm to pass through the first solid separation device 18e as a first liquid filtrate. The first solids separation device 18e includes one or more of a sieve, a gravity screen, a centrifuge, an auger press, or any other suitable dewatering device that removes particles larger than about 0.5 mm to 1.5 mm, or any combination thereof. The liquid filtrate portion of the slurry S that leaves the first solids separation device 18e can include fine particulate organic matter suspended in the liquid filtrate.

This first liquid filtrate then proceeds to a second solids separation process at step S20. In step S20, the first liquid filtrate from the first solids separation process is further processed in the second solids separation device $18_h$ to remove particles smaller than about 0.5 mm to 1.5 mm to produce a salable organic product 62 and a second liquid filtrate. The salable organic product 62 is described in greater detail below with reference to Table 1.

The second filtrate then undergoes, a second pH adjustment process in step S21 in the second pH adjustment section 18i. In the second pH adjustment step S21, the pH of the second filtrate is raised to a pH of between 8.5 and 11 to colloidize the soluble nutrients contained in the second filtrate in solution. For example, a caustic chemical (NaOH, KOH, $Mg(OH)_2$, $NH_3$ or similar) can be added to raise the pH of the second filtrate to suitable level to colloidize the soluble nutrients.

After the second pH adjustment step, the colloidal material of the second filtrate is removed in a third solids separation process S22. In the third solids separation process (water filtration process), a second solids separation device 18h is used again but this time to remove the colloidal material produced in step S21 to produce a nutrient enhanced media 63 and a third filtrate. The nutrient enhanced media 63 is described in greater detail below with reference to Table 1.

In an optional subsequent step S23 in the waste post-processing section, the membrane filtration process using the optional water filtration section 18k. can reduce the salinity of the third filtrate, resulting in a recyclable water 11 that is reintroduced into the organic waste treatment processing system 10.

Figure 13:
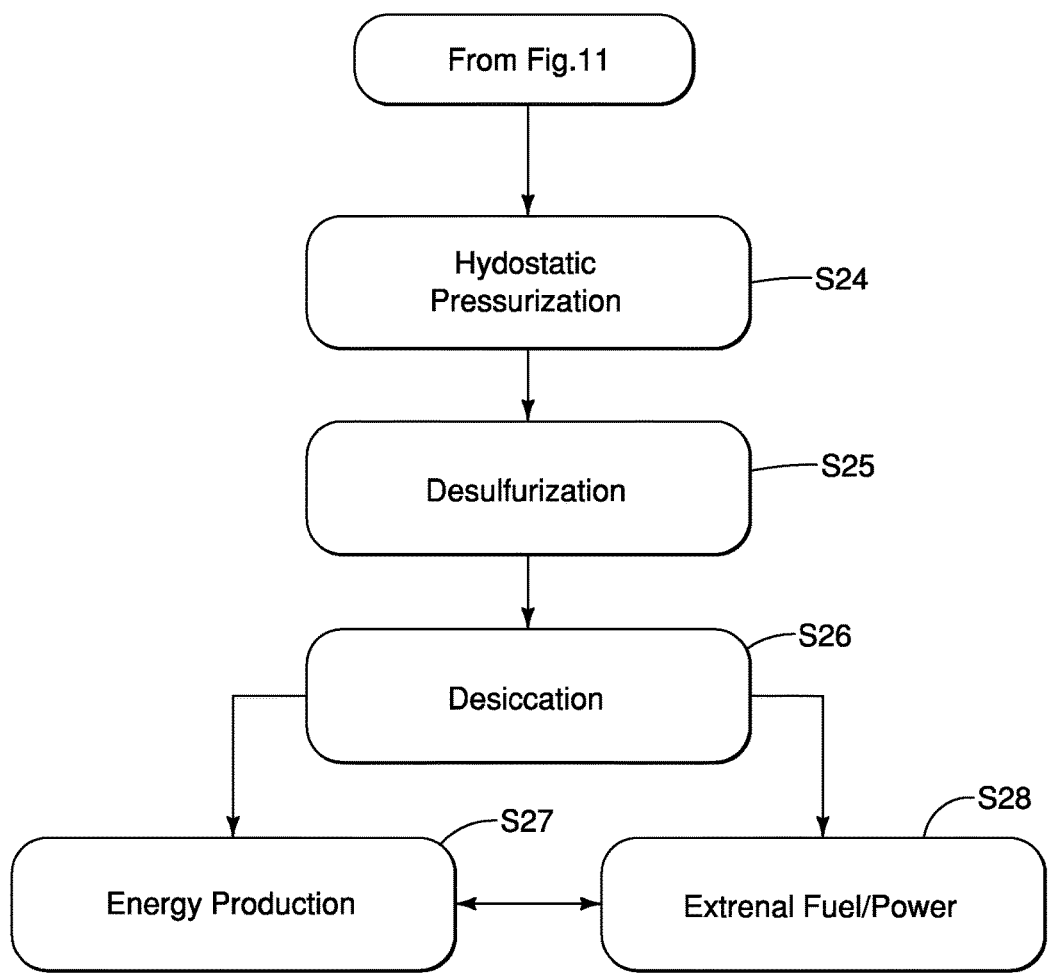
FIG. 13 is a fourth flowchart showing steps performed by the hydrocarbon vapor processing section in accordance with the first embodiment.

A description is now provided of the operations carried out by the hydrocarbon vapor processing section 20 with reference to FIG. 13. At step S24, the hydrocarbon vapors are captured and pressurized. At step S25, the hydrocarbon vapors undergo desulfurization. At step S26 the hydrocarbon vapors undergo desiccation to remove moisture. At step S27 the hydrocarbon vapors (compressed) are fed to electric generators (not shown) that produce electric power. The electric power can be used to power some or all of the electronic elements of the waste processing system 10. If sufficient electric power is produced at step S27 to run the entire waste processing system 10, any extra electricity can be sold and used to power external devices or can be supplied to a local electrical grid. Conversely, if insufficient electric power is produced at step S27 to run the entire waste processing system 10, electricity can be drawn from the local electrical grid.

Optional Processes

The first solid separation device 18e of the waste post processing section 18 can be configured to extract specific compounds and elements therefrom such as phosphorus, nitrogen, and/or other predetermined materials from the slurry using the methodology set forth in Applicant's U.S. Patent Application No. 62/215,859, which is hereby incorporated herein by reference in its entirety. Further, the second solid separation device 18h of the waste post processing section 18 can be configured to extract water from phosphorus-depleted slurry. The waste post processing section 18 can include a reactor and a reverse osmosis water extracting system that extracts water, nutrients, salts, metals, and organic/inorganic material from the remaining slurry materials.

Products

As mentioned above there are at least three categories of products that can be produced using the above. Applicants have compiled the data listed in Table 1 (below) that outlines the products.

TABLE 1

|  | Product 61 | | Product 62 | | Product 63 | |
| --- | --- | --- | --- | --- | --- | --- |
|  | Avg | StDev | Avg | StDev | Avg | StDev |
| As Sampled |  |  |  |  |  |  |
| Total Solids | 25.4% | 1.2% | 36.1% | 3.0% | 34.9% | 2.5% |
| Fixed Solids (% of TS) | 14.1% | 2.4% | 68.0% | 7.4% | 91.9% | 0.0% |

TABLE 1-continued

|  | Product 61 | | Product 62 | | Product 63 | |
| --- | --- | --- | --- | --- | --- | --- |
|  | Avg | StDev | Avg | StDev | Avg | StDev |
| Organic Carbon | 49.8% | 1.4% | 16.6% | 4.1% | 4.7% | 0.0% |
| Soluble Salts (ds/m) | 2.5 | — | 3.1 | 1.0 | 2.9 | 0.0 |
| C:N Ratio | 20.9 | — | 6.3 | 0.7 | 7.0 | 0.0 |
| Elemental N:P Ratio | 3.3 | 1.9 | 9.4 | 4.8 | 0.1 | 0.0 |
| Fertilizer N:P Ratio By Dry Weight | 1.5 | 0.8 | 4.1 | 2.1 | 0.1 | 0.0 |
| Total Nitrogen (TKN) | 0.9% | 1.3% | 2.9% | 0.5% | 0.7% | 0.1% |
| Total Phosphorus | 0.2% | 0.2% | 0.4% | 0.2% | 5.0% | 0.7% |
| Total Potassium | 0.3% | 0.3% | 0.6% | 0.3% | 0.4% | 0.1% |
| Sulfur | 0.5% | 0.6% | 1.3% | 0.6% | 0.4% | 0.1% |
| Calcium | 0.3% | 0.4% | 1.0% | 0.6% | 5.3% | 0.6% |
| Magnesium | 0.1% | 0.1% | 0.2% | 0.1% | 1.8% | 0.4% |
| Sodium | 0.1% | 0.1% | 0.4% | 0.1% | 0.5% | 0.1% |
| Zinc | 0.0% | 0.0% | 0.1% | 0.0% | 0.0% | 0.0% |
| Iron | 0.0% | 0.1% | 0.2% | 0.1% | 0.2% | 0.1% |
| Manganese | 0.0% | 0.0% | 0.0% | 0.0% | 0.2% | 0.1% |
| Copper | 0.0% | 0.0% | 0.1% | 0.0% | 0.0% | 0.0% |
| Aluminum | 0.0% | 0.0% | 0.1% | 0.0% | 0.0% | 0.0% |
| Boron | 0.0% | 0.0% | 0.0% | 0.0% | 0.0% | 0.0% |

As shown in Table 1 above, the stable organic material 61 produced in step S19 has a an Elemental nitrogen to phosphorus ratio (Elemental N:P Ratio) of 3.3:1±1.9 and a fertilizer ratio of nitrogen to phosphorus (Fertilizer N:P Ratio) of 1.5:1±0.8. The organic material 61 also contains approximately 0.5% by weight of sulfur on a dry basis and has an Elemental N:P:K:S ratio of 5:1:2:3.

Table 1 also shows that the salable organic product 62 produced in step S20 has an elemental ratio of nitrogen to phosphorus (Elemental N:P Ratio) of 9.4:1±4.8 and a fertilizer ratio of nitrogen to phosphorus (Fertilizer N:P Ratio) of 4.1:1±2.1. The salable organic product 62 also contains approximately 1.3% by weight of sulfur on a dry basis and has an Elemental N:P:K:S ratio of 7:1:1:3, while retaining organic carbon levels of 16.6%±4.1%.

As shown in Table 1 above, the nutrient enhanced media 63 produced in step S22 has an elevated level of phosphorus and calcium (5.0%±0.7% and 5.3%±0.6% on a dry weight basis, respectively) and an Elemental N:P:K:S ratio of 2:12:1:1, with a very low organic carbon composition of 4.7%.

Other Literature

Van Slyke (U.S. Pat. No. 6,916,426) discloses to extract ammonium, phosphorus and potassium from an animal waste slurry to form ureates of potassium and ammonium in crystalline form. Van Slyke further discloses that a substantial amount of potassium is extracted as ureates of potassium using flocculation before they degrade. Therefore, the solid material disclosed by Van Slyke contains substantial amounts of the potassium, nitrogen and phosphorus that were contained in the original animal waste sludge. Our fertilizer phosphorus product material is low in potassium (e.g., potassium content of less than 1%) and low in nitrogen (e.g., nitrogen content of less than 4) because the acid treatment that we apply with our process would solubilize and destroy the potassium ureates, and the potassium remains in solution in the liquid extract. Our subsequent alkaline addition to the liquid extract reaching a pH between 8 and 11 does not recover significant amounts of the solubilized potassium that resulted from the destruction of the potassium ureates at acid pH. Therefore, our phosphorus fertilizer product contains low concentrations of potassium. In contrast, our process does not involve ureates; there is also no flocculation of our initial animal wastes prior to or during our acid addition and/or lime addition.

The acidification of organic waste according to Szogi et al. (U.S. Pat. No. 8,673,046) is a three-part process that involves 1) phosphorus extraction, 2) phosphorus recovery, and 3) phosphorus recovery enhancement. These steps include the acidification of organic waste to a pH from 3.0-5.0, the settling of phosphorus depleted solids for removal from the waste stream, the precipitation of phosphorus by adjusting pH to between pH 8.0-11.0 using an alkaline earth based, and the removal of the precipitated phosphorus via settling and the addition of a flocculent. Our process differs in that it teaches the pretreatment and anaerobic digestion of organic material as a means of solubilizing nutrient and reducing pathogens in the original waste material. It further differs through the use of staged dewatering systems that, contrary to Szogi et al., seek to retain organic material beyond the first dewatering step in two distinct particle size fractions, and strictly avoids the use of coagulants or flocculants in any later-stage dewatering step. Critically, our process teaches the recycling of water from post-treatment to pretreatment.

Thus, in view of the above, the process of the present application concerns (in part) the following:

The various elements of the waste processing system 10 can be automated with electronically controlled valves, metering valves for accurately adding, for instance, acid, alkaline materials and/or water to the waste materials $M_O$ and slurry, sensors for detecting, for example, temperature and pH, pumps, grinders, and other slurry and waste processing equipment. The automated control of the portions of the waste processing system 10 can be operated by a controller (not show). The controller preferably includes a microcomputer with a control program that controls the various sections of the waste processing system 10, as discussed below. The controller can also include other conventional components such as an input interface circuit, an output interface circuit, and storage devices such as a ROM (Read Only Memory) device and a RAM (Random Access Memory) device. The microcomputer of the controller is programmed to control the waste processing system 10. The memory circuit stores processing results and control programs such as ones for waste processing system operation that are run by the processor circuit. The controller is operatively coupled to the various elements of the waste processing system 10 in a conventional manner. The controller is capable of selectively controlling any of the components of the waste processing system 10 in accordance with the control program. It will be apparent to those skilled in the art from this disclosure that the precise structure and algorithms for the controller can be any combination of hardware and software that will carry out the functions of the present invention.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of a vehicle equipped with the waste processing system. Accordingly, these terms, as utilized to describe the present invention should be interpreted relative to a vehicle equipped with the waste processing system.

The term "detect" as used herein to describe an operation or function carried out by a component, a section, a device or the like includes a component, a section, a device or the like that does not require physical detection, but rather includes determining, measuring, modeling, predicting or computing or the like to carry out the operation or function.

The term "configured" as used herein to describe a component, section or part of a device includes hardware and/or software that is constructed and/or programmed to carry out the desired function.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature that is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for the purpose of limiting the invention as defined by the appended claims and their equivalents.

What is claimed is:

1. A method of treating organic waste, the method comprising:
   combining organic waste materials including one or more of manure, food waste or crop waste with water in a waste material holding tank;
   homogenizing the organic waste material and water while within the waste material holding tank producing a slurry reducing particle size of solids to no greater than 25 mm;
   pumping the slurry from the waste material holding tank to at least one preparation tank;
   heating the slurry within the at least one preparation tank to a predetermined temperature between 15° C. and 40° C.;
   digesting the slurry and capturing hydrocarbon vapors given off from digested slurry;
   producing electricity from the captured hydrocarbon vapors thereby providing power to devices that effect the homogenizing of the organic waste material and heating of the slurry;
   decreasing the pH of the digested slurry;
   selectively separating solids according to size in a first solids separation process to produce a first salable organic product and a first liquid filtrate;
   selectively separating solids according to size in a second solids separation process to produce a second salable organic product and a second liquid filtrate;
   increasing the pH of the second liquid filtrate;
   selectively separating solids according to size in a third solids separation process to produce a salable fertilizer product and recyclable water; and
   using the recyclable water in the combining of the organic waste materials with water.

2. The method of treating organic waste, according to claim 1, the method further comprising
   the homogenizing of the organic waste material includes at least one of the following operations performed on the organic waste material:
   passing the organic waste material through a grinder;
   passing the organic waste material through a shredder; and
   passing the organic waste material through a hammer mill.

3. The method of treating organic waste, according to claim 1, wherein the heating of the slurry to a predetermined temperature includes heating of the slurry to a temperature between 25° C. and 40° C.

4. The method of treating organic waste, according to claim 1, wherein
   the digesting of the slurry and capturing hydrocarbon vapors given off from the slurry includes a first anaerobic digestion process and a second anaerobic digestion process.

5. The method of treating organic waste, according to claim 4, wherein
   the first anaerobic digestion process includes feeding the slurry into a pressurizeable tank and adjusting the slurry to the predetermined temperature in order to promote microbially-facilitated hydrolysis and acidogenesis to produce the hydrocarbon vapors.

6. The method of treating organic waste, according to claim 5, wherein
   the second anaerobic digestion process includes moving the slurry from the pressurizeable tank to another pressurizeable tank where the slurry undergoes further biological degradation at the predetermined temperature in order to reduce total solids and odor and mineralize nutrients and metals in the slurry.

7. The method of treating organic waste, according to claim 1, wherein
   the decreasing the pH of the digested slurry includes use of mineral acids including at least one of $H_2SO_4$, HCl, or combinations of mineral and organic acids being added to the digested slurry material in a pressurizeable and/or temperature adjusted tank or a plurality of such tanks until the pH is at or below 6.0.

8. The method of treating organic waste, according to claim 7, wherein the first solids separation process includes particulate matter inherent in the slurry and larger than about 0.5-1.5 mm being removed via sieves, gravity screens, centrifuges, auger presses, or other dewatering devices to produce a stable, dewatered organic material and a filtrate.

9. The method of treating organic waste, according to claim 8, wherein
the second solids separation process includes the addition of a filtration aid, in which particulate matter smaller than about 0.5-1.5 mm is removed using a mechanical or membrane-based dewatering device to produce the second salable organic product and the second filtrate.

10. The method of treating organic waste, according to claim 9, wherein
the second filtrate is subjected to a second pH adjustment process in which the pH is adjusted above pH 7 with a caustic chemical in a pressurizable and/or temperature adjustable tank or plurality of such tanks to increase nutrient content and colloidize the soluble nutrients in solution, and
the second filtrate is then subjected to a third solids separation process in which the colloidal material is removed using a mechanical or membrane-based dewatering device to produce a nutrient enhanced media and the recyclable water, which is then either reintroduced into a waste treatment process, used as a fertilizer, or directed towards a further membrane filtration process in which the salinity is reduced, resulting in recyclable water.

11. A method of treating an anaerobically digested slurry, the method comprised of:
decreasing the pH of the anaerobically digested slurry, thereby solubilizing nutrients and reducing pathogenicity in the slurry;
selectively separating solids according to size in a first solids separation process to form a first anaerobically digested liquid filtrate and a high C:N ratio stable organic material, where C represents carbon and N represents nitrogen and the C:N ratio is at least 6:1;
selectively separating solids in the first anaerobically digested liquid filtrate according to size in a second solids separation process to form a second anaerobically digested liquid filtrate and a high N:P ratio salable organic product, where N represents nitrogen and P represents phosphorus and the N:P ratio is at least 4:1;
increasing the pH of the second anaerobically digested liquid filtrate, thereby precipitating phosphorus with an organic content of no greater than 4.7%; without the use of flocculants;
selectively separating solids according to size in a third solids separation process to form a nutrient enhanced media having a phosphorus content of about 5% and a third anaerobically digested liquid filtrate.

12. The method of treating the anaerobically digested slurry, according to claim 11, wherein the pH of the anaerobically digested slurry is decreased using mineral acids including at least one of $H_2SO_4$, HCl, or combinations of mineral and organic acids until the pH is at or below 6.0.

13. The method of treating the anaerobically digested slurry, according to claim 12, wherein after subjecting the anaerobically digested slurry to the decreasing of the pH, the anaerobically digested slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and a first liquid filtrate.

14. The method of treating the anaerobically digested slurry, according to claim 12, wherein an anti-foaming reagent is added to the anaerobically digested slurry.

15. The method of treating the anaerobically digested slurry, according to claim 11, wherein the pH of the anaerobically digested slurry is decreased using mineral acids including at least one of $H_2SO_4$, HCl, or combinations of mineral and organic acids until the pH is at or below 5.0.

16. The method of treating the anaerobically digested slurry, according to claim 15, wherein after subjecting the anaerobically digested slurry to the decreasing of the pH, the anaerobically digested slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and a first liquid filtrate.

17. The method of treating the anaerobically digested slurry, according to claim 15, wherein an anti-foaming reagent is added to the anaerobically digested slurry.

18. The method of treating the anaerobically digested slurry, according to claim 17, wherein the dewatering device is the same device used to produce the salable organic products in the second solids separation process.

19. The method of treating the anaerobically digested slurry, according to claim 11, wherein the pH of the anaerobically digested slurry is decreased using mineral acids including at least one of $H_2SO_4$, HCl, or combinations of mineral and organic acids until the pH is 4.0.

20. The method of treating the anaerobically digested slurry, according to claim 19, wherein after subjecting the anaerobically digested slurry to the decreasing of the pH, the anaerobically digested slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and a first liquid filtrate.

21. The method of treating the anaerobically digested slurry, according to claim 19, wherein an anti-foaming reagent is added to the anaerobically digested slurry.

22. The method of treating the anaerobically digested slurry, according to claim 11, wherein an anti-foaming reagent is added to the anaerobically digested slurry.

23. The method of treating the anaerobically digested slurry, according to claim 11, wherein the pH is adjusted in a pressurizeable and/or temperature adjusted tank or a plurality of such tanks.

24. The method of treating the anaerobically digested slurry, according to claim 23, wherein said tanks are mixed or agitated.

25. The method of treating the anaerobically digested slurry, according to claim 11, wherein after the second solids separation process and the increasing of the pH of the second liquid filtrate, the second liquid filtrate is processed in the third solids separation process in which particulate matter is removed using a mechanical or membrane-based dewatering device to produce a nutrient enhanced media and the third liquid filtrate.

26. The method of treating the anaerobically digested slurry, according to claim 11, wherein the first solids separation process is such that particulate matter in the anaerobically digested slurry larger than about 0.5-1.5 mm is removed via at least one of sieves, gravity screens, centrifuges, auger presses, or other dewatering devices to produce a stable, anaerobically digested, dewatered, organic material and the first anaerobically digested liquid filtrate.

27. The method of treating the anaerobically digested slurry, according to claim 26, wherein the first solids separation process produces an organic material with an elemental nitrogen to phosphorus ratio of at least a 5:1.

28. The method of treating the anaerobically digested slurry, according to claim 27, wherein the pH of the second anaerobically digested liquid filtrate is increased using caustic chemicals including at least one of NaOH, KOH, $Mg(OH)_2$, or combinations of alkali bases until the pH is at or above 7.0.

29. The method of treating the anaerobically digested slurry, according to claim 26, wherein the second solids separation process is facilitated by the addition of a filtration aid, in which particulate matter smaller than about 0.5-1.5 mm is removed using a mechanical or membrane-based dewatering device to produce the salable organic product and the second anaerobically digested liquid filtrate.

30. The method of treating the anaerobically digested slurry, according to claim 29, wherein the pH of the second anaerobically digested liquid filtrate is increased using caustic chemicals including at least one of NaOH, KOH, Mg(OH)2, or combinations of alkali bases until the pH is at or above 8.5.

31. The method of treating the anaerobically digested slurry, according to claim 29, wherein the pH of the second anaerobically digested liquid filtrate is increased using caustic chemicals including at least one of NaOH, KOH, Mg(OH)2, or combinations of alkali bases until the pH is at or above 9.0.

32. The method of treating the anaerobically digested slurry, according to claim 29, wherein the pH of the second anaerobically digested liquid filtrate is increased using caustic chemicals including at least one of NaOH, KOH, Mg(OH)2, or combinations of alkali bases until the pH is at or above 10.0.

33. The method of treating the anaerobically digested slurry, according to claim 29, wherein the second solids separation process produces an organic material with an elemental nitrogen to phosphorus ratio of at least a 5:1.

34. The method of treating the anaerobically digested slurry, according to claim 29, wherein the second solids separation process produces an organic material with an elemental nitrogen to phosphorus ratio of at least a 6:1.

35. The method of treating the anaerobically digested slurry, according to claim 29, wherein the second solids separation process produces an organic material with an elemental nitrogen to phosphorus ratio of at least a 7:1.

36. The method of treating the anaerobically digested slurry, according to claim 29, wherein the second solids separation process produces an organic material with an elemental nitrogen to phosphorus ratio of at least an 8:1.

37. The method of treating the anaerobically digested slurry, according to claim 29, wherein the second solids separation process produces an organic material with an elemental nitrogen to phosphorus ratio of at least a 9:1.

38. The method of treating the anaerobically digested slurry, according to claim 29, wherein after the second solids separation process, the second anaerobically digested liquid filtrate is processed in the third solids separation process in which particulate matter is removed using a mechanical or membrane-based dewatering device to produce a nutrient enhanced media and the third anaerobically digested liquid filtrate.

39. The method of treating the anaerobically digested slurry, according to claim 38, wherein the third solids separation process produces a nutrient enhanced media with an elemental phosphorus content of at least a 4.5% by dry weight.

40. The method of treating the anaerobically digested slurry, according to claim 38, wherein the third solids separation process produces a nutrient enhanced media with an elemental phosphorus content of at least a 5.0% by dry weight.

41. The method of treating the anaerobically digested slurry, according to claim 38, wherein the third solids separation process produces a nutrient enhanced media with an elemental phosphorus content of at least a 5.7% by dry weight.

42. The method of treating the anaerobically digested slurry, according to claim 38, wherein the third anaerobically digested liquid filtrate is further processed with a water filtration system that includes a reverse osmosis apparatus.

43. A method of treating an organic waste slurry comprised of:
decreasing the pH of the organic waste slurry, thereby solubilizing nutrients and reducing pathogenicity in the organic waste slurry;
selectively separating solids in the organic waste slurry according to size in a first solids separation process to form a first liquid filtrate and a high C:N ratio stable organic material, where C represents carbon and N represents nitrogen and the C:N ratio is at least 6:1;
selectively separating solids in the first liquid filtrate according to size in a second solids separation process to form a second filtrate and a high N:P ratio salable organic product, where N represents nitrogen and P represents phosphorus and the N:P ratio is at least 4:1;
increasing the pH of the second liquid filtrate, thereby precipitating phosphorus with an organic content no greater than 4.7% without the use of flocculants;
selectively separating solids according to size in a third solids separation process to form a nutrient enhanced media having a phosphorus content of about 5% and a third filtrate.

44. The method of treating the organic waste slurry, according to claim 43, wherein the decreasing of the pH of the organic waste slurry includes using mineral acids including at least one of $H_2SO_4$, HCl, or combinations of mineral and organic acids until the pH is at or below 6.0.

45. The method of treating the organic waste slurry, according to claim 44, wherein after subjecting the organic waste slurry to the decreasing of the pH, the organic waste slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and the first liquid filtrate.

46. The method of treating the organic waste slurry, according to claim 43, wherein the decreasing of the pH of the organic waste slurry includes using mineral acids including at least one of $H_2SO_4$, HCl, or combinations of mineral and organic acids until the pH is at or below 5.0.

47. The method of treating the organic waste slurry, according to claim 46, wherein after subjecting the organic waste slurry to the decreasing of the pH, the organic waste slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and the first liquid filtrate.

48. The method of treating the organic waste slurry, according to claim 43, wherein the decreasing of the pH of the organic waste slurry includes using mineral acids including at least one of $H_2SO_4$, HCl, or combinations of mineral and organic acids until the pH is 4.0.

49. The method of treating the organic waste slurry, according to claim 48, wherein after subjecting the organic waste slurry to the decreasing of the pH, the organic waste slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and the first liquid filtrate.

50. The method of treating the organic waste slurry, according to claim 43, wherein an anti-foaming reagent is added to the organic waste slurry.

51. The method of treating the organic waste slurry, according to claim 50, wherein after subjecting the organic waste slurry to the decreasing of the pH, the organic waste slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and the first liquid filtrate.

52. The method of treating the organic waste slurry, according to claim 43, wherein the decreasing of the pH is adjusted in a pressurizeable and/or temperature adjusted tank or a plurality of such tanks.

53. The method of treating the organic waste slurry, according to claim 52, wherein after subjecting the organic waste slurry to the decreasing of the pH, the organic waste slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and the first liquid filtrate.

54. The method of treating the organic waste slurry, according to claim 52, wherein the pressurizeable and/or temperature adjusted tanks are mixed or agitated.

55. The method of treating the organic waste slurry, according to claim 43, wherein after subjecting the organic waste slurry to the decreasing of the pH of the organic waste slurry, the organic waste slurry is further processed by the first solids separation process in which particulate matter inherent in the organic waste slurry and larger than about 0.5-1.5 mm is removed via sieves, gravity screens, centrifuges, auger presses, or other dewatering devices to produce a stable, anaerobically digested, dewatered, organic material and the first liquid filtrate.

56. The method of treating the organic waste slurry, according to claim 55, wherein the first solids separation process produces an organic material with an elemental nitrogen to phosphorus ratio of at least a 5:1.

57. The method of treating the organic waste slurry, according to claim 55, wherein after the first solids separation process, the first liquid filtrate is processed in a second solids separation process facilitated by the addition of a filtration aid, in which particulate matter smaller than about 0.5-1.5 mm is removed using a mechanical or membrane-based dewatering device to produce a salable organic product and the second liquid filtrate.

58. The method of treating the organic waste slurry, according to claim 57, wherein the increasing of the pH of the second liquid filtrate includes using caustic chemicals including at least one of NaOH, KOH, Mg(OH)2, or combinations of alkali bases until the pH is at or above 7.0.

59. The method of treating the organic waste slurry, according to claim 57, wherein the increasing of the pH of the second liquid filtrate includes using caustic chemicals including at least one of NaOH, KOH, Mg(OH)2, or combinations of alkali bases until the pH is at or above 8.5.

60. The method of treating the organic waste slurry, according to claim 57, wherein the increasing of the pH of the second liquid filtrate includes using caustic chemicals including at least one of NaOH, KOH, Mg(OH)2, or combinations of alkali bases until the pH is at or above 9.0.

61. The method of treating the organic waste slurry, according to claim 57, wherein the increasing of the pH of the second liquid filtrate includes using caustic chemicals including at least one of NaOH, KOH, Mg(OH)2, or combinations of alkali bases until the pH is at or above 10.0.

62. The method of treating the organic waste slurry, according to claim 61, wherein the second solids separation process produces an organic material with an elemental nitrogen to phosphorus ratio of at least a 5:1.

63. The method of treating the organic waste slurry, according to claim 57, wherein the second solids separation process produces an organic material with an elemental nitrogen to phosphorus ratio of at least a 6:1.

64. The method of treating the organic waste slurry, according to claim 57, wherein the second solids separation process produces an organic material with an elemental nitrogen to phosphorus ratio of at least a 7:1.

65. The method of treating the organic waste slurry, according to claim 57, wherein the second solids separation process produces an organic material with an elemental nitrogen to phosphorus ratio of at least an 8:1.

66. The method of treating the organic waste slurry, according to claim 57, wherein the second solids separation process produces an organic material with an elemental nitrogen to phosphorus ratio of at least a 9:1.

67. The method of treating the organic waste slurry, according to claim 57, wherein after the second solids separation process and the increasing of the pH of the second liquid filtrate, the second liquid filtrate is processed in a third solids separation process in which particulate matter is removed using a mechanical or membrane-based dewatering device to produce a nutrient enhanced media and the third liquid filtrate.

68. The method of treating the organic waste slurry, according to claim 67, wherein the dewatering device is the same device used to produce the salable organic product.

69. The method of treating the organic waste slurry, according to claim 67, wherein the third solids separation process produces a nutrient enhanced media with an elemental phosphorus content of at least a 4.5% by dry weight.

70. The method of treating the organic waste slurry, according to claim 67, wherein the third solids separation process produces a nutrient enhanced media with an elemental phosphorus content of at least a 5.0% by dry weight.

71. The method of treating the organic waste slurry, according to claim 67, wherein the third solids separation process produces a nutrient enhanced media with an elemental phosphorus content of at least a 5.7% by dry weight.

72. The method of treating the organic waste slurry, according to claim 67, wherein the third liquid filtrate is further processed with a water filtration system that includes a reverse osmosis apparatus.

* * * * *